United States Patent [19]

Haviv et al.

[11] Patent Number: 5,698,522
[45] Date of Patent: Dec. 16, 1997

[54] 6-POSITION MODIFIED DECAPEPTIDE LHRH ANTAGONISTS

[75] Inventors: Fortuna Haviv, Deerfield, Ill.;
Timothy D. Fitzpatrick, Salem, Oreg.;
Rolf E. Swenson, Grayslake, Ill.;
Charles J. Nichols, Greendale, Wis.;
Nicholas A. Mort, Waukegan;
Jonathan Greer, Chicago, both of Ill.

[73] Assignee: Abbott Laboratories, Abbott Park, Ill.

[21] Appl. No.: 446,809

[22] PCT Filed: Nov. 30, 1993

[86] PCT No.: PCT/US93/11628

§ 371 Date: Jun. 1, 1995

§ 102(e) Date: Jun. 1, 1995

[87] PCT Pub. No.: WO94/13313

PCT Pub. Date: Jun. 23, 1994

Related U.S. Application Data

[63] Continuation of Ser. No. 987,921, Dec. 4, 1992, abandoned.
[51] Int. Cl.$^6$ .............................. A61K 38/09; C07K 7/23
[52] U.S. Cl. ........................... 514/15; 530/313; 530/328
[58] Field of Search ................................. 530/313, 328; 514/15

[56] References Cited

U.S. PATENT DOCUMENTS 5,110,904  5/1992  Haviv et al. ......................... 530/313

OTHER PUBLICATIONS

Dayhoff, M. 'Atlas of Protein Sequence and Structure 1972', Wash. D.C.:National Biomedical Research Foundation, vol. 5, p. 76, 1972.

Schulz et al. 'Principles of Proetin Structure', New York: Springer–Verlag, pp. 14–16, 1979.

Ljungquist, Anders et al. Z. Naturforsch., B: Chem. Sci. 46(9), 1231–6 Article Title Design, Synthesis & Biological Evaluation of Antagonists of LHRH Criteria of Potency, Safety & Solubility, 1991.

Primary Examiner—Cecilia J. Tsang
Assistant Examiner—Anish Gupta
Attorney, Agent, or Firm—Mona Anand

[57] ABSTRACT

The present invention provides a class of decapeptide compounds which are potent antagonists of LHRH activity and which have the structure $A^1-D^2-E^3-G^4-J^5-L^6-M^7-Q^8-R^9-T^{10}$. The compounds of the percent invention are characterized by having an $\Omega$-amino-functionalized side chain on the D-aminoacyl residue at position 6. The $\Omega$-amino group of this side chain is further derivatized by the attachment of an extending group which likewise has a terminal amino group which is capped by an acyl group.

6 Claims, No Drawings

6-POSITION MODIFIED DECAPEPTIDE LHRH ANTAGONISTS

CROSS REFERENCES TO RELATED APPLICATIONS

This application is a 371 application of PCT/US93/11628 which is continuation of U.S. patent application Ser. No. 07/987,921 filed Dec. 4, 1992 and now abandoned.

TECHNICAL FIELD

The present invention relates to peptides having pharmacological activity, to pharmaceutical compositions containing such peptides, and to a medical method of treatment.

More particularly, the present invention coheres certain decapeptides, modified in the 6-position which are antagonists of luteinizing-hormone-releasing-hormone (LHRH), to pharmaceutical compositions containing these peptides, and to a method of inhibiting LHRH activity in a mammal in need of such treatment.

BACKGROUND OF THE INVENTION

The gonadotropins, follicle stimulating hormone (FSH), luteinizing hormone (LH), and chorionic gonadotropin (CG) are required for ovulation, spermatogenesis, and the biosynthesis of sex steroids. A single hypothalamic hormone, gonadotmpin-releasing-hormone (GnRH, also known as luteinizing-hormone-releasing-hormone, LHRH) is responsible for regulating the secretion of both FSH and LH in mammals.

LHRH has the structure pyro-Glu$^1$-His$^2$-Trp$^3$-Ser$^4$-Tyr$^5$-Gly$^6$-Leu$^7$-Arg$^8$-Pro$^9$-Gly$^{10}$-NH$_2$ where the superscripts designate the position of each aminoacyl residue in the decapeptide chain.

LHRH is released from the hypothalamus and binds to a receptor on the pituitary gland, causing the release of LH and FSH which subsequently act on the gonads to stimulate the synthesis of steroid sex hormones. The pulsatile release of LHRH, and thereby the release of LH and FSH, controls the reproductive cycle in animals and man. Acute doses of LHRH agonists increase the levels of LH and steroidal sex hormones in both animals and humans. Paradoxically, chronic doses of LHRH agonists suppress the levels of LH and steroidal sex hormones. Consequently, the effect of multiple doses of LHRH agonists is to suppress estrogen formation in females and testosterone production in males. The same effect is observed in both animals and humans after administration of either acute or chronic doses of LHRH antagonism.

In recent years considerable research effort has been expended on finding synthetic analogs of LHRH. These efforts have produced a number of LHRH agonists and antagonists, with considerable research being devoted to finding peptides which mimic the anti-ovulatory potency of LHRH while minimizing undersirable side-effects such as stimulation of histidine release.

SUMMARY OF THE INVENTION

The present invention provides a class of decapeptide compounds which are potent antagonists of LHRH activity and which are characterized by having an Ω-amino-functionalized side chain on the D-aminoacyl residue at position 6. The Ω-amino group of this side chain is further derivatized by the attachment of an extending group which likewise has a terminal amino group which is capped by an acyl group. In particular, the present invention provides a peptide or pharmaceutically aceaeptable salt thereof of the formula

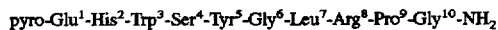

wherein A is an aminoacyl residue selected from the group consisting of N-acetyl-D-3-(naphth-2-yl)alanyl; N-acetyl-D-phenylalanyl; N-acetyl-D-3-(4-hlorophenyl)alanyl; N-acetyl-D-3-(quinolin-3-yl)alanyl; N-acetyl-azaglycyl, and N-acetylsacrosyl.

The second aminoacyl residue in the decapeptide chain, D, is selected from the group consisting of D-phenylalanyl; D-3-(4-chlorophenyl)alanyl; D-3-(4-fluorophenyl)alanyl; and D-3-(naphth-2-yl)alanyl.

The residue E is selected from the group consisting of D-3-(pyrid-3-yl)alanyl; D-3-(naphth-1-yl)alanyl; N-acetyl-D-3-(quinolin-3-yl)alanyl, D-3-(thiazol-2-yl)alanyl; and D-3-(benzo[b]thien-2-yl)alanyl.

G is an aminoacyl residue selected from the group consisting of L-seryl; L-seryl(O-benzyl); and N(R$^1$)-L-seryl where R$^1$ is hydrogen or alkyl of from one to four carbon atoms.

The fifth aminoacyl residue in the decapeptide chain, J, is selected from the group consisting of N(R$^1$)-L-[3-(4-(3-amino-1,2,4-triazol-5-yl)aminophenyl)]alanyl; N(R$^1$)-L-[3-(4-(3-amino-1,2,4-triazol-5-yl)aminocyclohexyl)]alanyl; N(R$^1$)-L-[3-(4-nicotinyl)aminocyclohexyl)]alanyl; N(R$^1$)-[N-epsilon-nicotinyl]-L-lysyl; N(R$^1$)-[N-epsilon-(3-amino-1,2,4-triazol-5-yl)]L-lysyl; N(R$^1$)-L-[3-(4-nitrophenyl)]alanyl; L-[3-(4-aminophenyl)]alanyl; L-[3-(4-aminocyclohexyl)]alanyl; N(R$^1$)-L-tyrosyl; N(R$^1$)-L-tyrosyl(O-methyl); N(R$^1$)-L-Phenylalanyl; N(R$^1$)-L-cyclohexylalanyl; N(R$^1$)-L-arginyl; and N(R$^1$)-L-homoarginyl; where R$^1$ is as defined above.

L is a D-aminoacyl residue having the structure

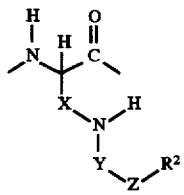

where X is selected from the group consisting of —(CH$_2$)$_n$— where n is an integer of from one to six, inclusive, and

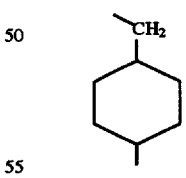

Y is an aminoacyl residue selected from the group consisting of D-alanyl; L-alanyl; 4-aminobutyryl; 5-aminopentanoyl; 6-aminohexanoyl; 7-aminoheptanoyl; 8-aminooctanoyl; 11-aminoundecanoyl; azaglycyl; D-3-(benzo[b]thien-2-yl)alanyl; D-3-(4-chlorophenyl)alanyl; D-cyclohexylalanyl; glycyl; D-histidyl; D-histidyl(benzyl); D-leucyl; D-3-(naphth-2-yl)alanyl; D-3-(naphth-2-yl) alanyl; D-phenylalanyl; D-3-(pyrid-3-yl)alanyl; sarcosyl; L-seryl; D-seryl; D-threonyl; D-3-(thiazol-4-yl)alanyl; D-tryptyl; D-tyrosyl; D-tyrosyl(O-methyl); D-valyl; and L-3-(benzo[b]thien-2-yl)alanyl.

Z is absent or is an aminoacyl residue selected from the group consisting of D-alanyl; L-alanyl; azaglycyl; D-cyclohexylalanyl; glycyl; D-histidyl; D-phenylalanyl; D-3[-4-(3-amino-1,24-triazol-5-yl)phenyl]alanyl; sarcosyl; D-seryl; L-seryl; and

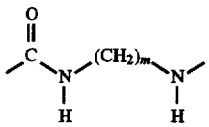

where M is an integer of from one to twelve, inclusive.

The group $R^2$ is 3-amino-1,2,4-triazol-5-yl or is an acyl group selected from the group consisting of acetyl; biotinyl (i.e. hexahydro-2-oxo-1H-thieno[3,4-d]imidazole-4-pentanoyl), (4-acetylpiperazin-1-yl)carbonyl; (adamant-1-yl)carbonyl; benzoyl, optionally substituted with a group selected from alkyl of one to four carbon atoms, alkoxy of one to four carbon atoms, and halogen; butyryl; cycolhexylcarbonyl; dihydroshikimyl; formyl; 2-furoyl; 2- and 6-hydroxynicotinyl; (indolyl)carbonyl; isonicotinyl; (4-methylpiperazin-1-yl)carbonyl; (morphilin-1-yl)carbonyl; 2- and 6-methylnicotinyl; 1- and 2-naphthoyl optionally substituted; with a group selected from alkyl of one to four carbon atoms; alkoxy of one to four arbon atoms, and halogen; picolyl; piperazin-1-yl)carbonyl; propionyl, pyrazinoyl; pyridylacetyl; (pyrrolyl)carbony; (quinolinyl)carbony; salicilyl; shikimyl; 2-(tetrahydrofuroyl), and (thien-2-yl)carbonyl.

The seventh aminoacyl residue in the decapeptides of this invention, M, is selected from the group consisting of L-leucyl; $N(R^1)$-L-leucyl; L-valyl; L-cyclohexylalanyl; and $N(R^1)$-L-cyclohexylalanyl; where $R^1$ is as defined above.

Q is an aminoacyl residue selected from the group consisting of L-citrullyl; L-homocitrullyl; L-(epsilon-N-isopropyl)lysyl; L-arginyl; and $N(R^1)$-L-arginyl; L-homoarginyl; L-2-amino-6-$N^G$-ethylguanidinohexanoyl; and L-2-amino-6-$N^G,N^G$ diethylguanidinohexanoyl.

R is an aminoacyl residue selected from the group consisting of L-prolyl; and $N(R^1)$-L-alanyl; where $R^1$ is as defined above; and T is —$NH(CH_2CH_3)$ or is an aminoacyl residue selected from the group consisting of D-alanylamide, $N(R^1)$-L-alanylamide, $N(R^1)$-D-alanylamide, sarcosamide, D-serylamide, and azaglycylamide, where $R^1$ is as defined above and with the proviso that when T is —$NH(CH_2CH_3)$ then R is L-prolyl.

DETAILED DESCRIPTION

In the decapeptides of the present invention the preferred value for the aminoacyl residue, A, is N-acetyl-3-(naphth-2-yl)-D-alanyl, designated "NAc-D-2-Nal". The preferred value for D is 3-(4-chlorophenyl)-D-alanyl or "D4ClPhe."

The preferred value for E is 3-(pyrid-3-yl)-D-alanyl or "D3Pal." Preferred values for J are L-3-(4-(3-amino-1,2,4-triazol-5-yl)aminophenyl)alanyl; L-3-(4-(3-amino-1,2,4-triazol-5-yl)aminocyclohexyl)alanyl; L-3-(4-nicotinyl)aminocyclohexyl)alanyl; L-3-(4-aminophenyl)alanyl; L-3-(4-aminocyclohexyl)alanyl; $N(R^1)$-L-tyrosyl; where $R^1$ is alkyl of from one to four carbon atoms. Particularly preferred at position 5 is the aminoacyl residue N-methyl-L-tyrosyl or "NMeTyr."

At position six of the decapeptides of this invention, compounds which are preferred are those in which the extending group Z is absent. For the side-chain group X, a lysyl side-chain is most preferred.

For the group Y, preferred groups are glycyl and azaglycyl, L-seryl, D-seryl, γ-aminobutyryl, aminoveleryl (i.e. 5-aminopentanoyl), aminocaproyl (i.e. 6-aminohexanoyl), and 7-aminoheptanoyl, with glycyl and azaglycyl being particularly preferred.

Preferred acyl end-tapping groups for $R^2$ include nicotinyl, furoyl, tetrahydrofuroyl, and shikimyl, with nicotinyl and furoyl being particularly preferred.

The preferred value for the aminoacyl residue, M, is L-leucyl, and for Q, it is N-epsilon-isopropyl-L-lysyl. The preferred value for R is L-prolyl, and for T it is D-alaninamide.

Particularly preferred individual compounds of the present invention are (N-acetyl-D-3-(naphth-2-yl)alanyl)[1]-(D-3-(4-chlorophenyl)alanyl)[2]-(D-3-(pyridin-3-yl)alanyl[3]-(L-seryl)[4]-(N-methyl-tyrosyl)[5]-(N-epsilon-(nicotinylglycyl)-D-lysyl)[6]-(L-leucyl)[7]-(N-epsilon-isopropyl(L-lysyl))[8]-(L-prolyl)[9]-D-alaninamide)[10]; (N-acetyl-D-3-(naphth-2-yl)alanyl)[1]-(D-3-(4-chlorophenyl)alanyl)[2]-(D-3-(pyridin-3-yl)alanyl[3]-(L-seryl)[4]-(N-methyl-tyrosyl)[5]-(N-epsilon-(nicotinylazaglycyl)-D-lysyl)[6]-(L-leucyl)[7]-(N-epsilon-isopropyl(L-lysyl))[8]-(L-prolyl)[9]-D-alaninamide)[10]; (N-acetyl-D-3-(naphth-2-yl)alanyl)[1]-(D-3-(4-chlorophenyl)alanyl)[2]-(D-3-(pyridin-3-yl)alanyl[3]-(L-seryl)[4]-(N-methyltyrosyl)[5]-(N-epsilon-(2-furoylglycyl)-D-lysyl)[6]-(L-leucyl)[7]-(N-epsilon-isopropyl(L-lysyl))[8]-(L-prolyl)[9]-D-alaninamide)[10]; and (N-acetyl-D-3-(naphth-2-yl)alanyl)[1]-(D-3-(4-chlorophenyl)alanyl)[2]-(D-3-(pyridin-3-yl)alanyl[3]-(L-seryl)[4]-(N-methyl-tyrosyl)[5]-(N-epsilon-(2-furoylazaglycyl)-D-lysyl)[6]-(L-leucyl)[7]-(N-epsilon-isopropyl(L-lysyl))[8]-(L-prolyl)[9]-D-alaninamide)[10].

As used throughout this specification and the appended claims, the following terms and abbreviations having the meaningsascribed to them below.

For the most part, the names of natururally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)," *Biochemistry*, 14 (2): 1975), which is incorporated herein by reference. To the extent that the names and abbreviations employed in this specification and appended claims differ from those suggestions, they will be made clear to the reader by the following table.

The term "aminoacyl residue" or "amino acid" is intended to denote both the naturally-occuring L-amino acids as well as their non-natural D-enantiomers. The term is also applied herein to compounds which bear both amino and carbnoxyl functional groups and which are correctly named "amino acids" but which are not members of the set of naturally occuring amino acids. Such compounds include, for example, D- and L-3-(4-aminocyclohexyl/)alanine, 7-aminoheptanoic acid, and similar amino acids.

TABLE 1

Amino Acyl Residue Abbreviations

| Abbreviation | Definition |
|---|---|
| | Alanyl & Derivatives |
| Ala | L-Alanyl |
| D-Ala | D-Alanyl |
| L-AlaNH2 | L-Alanylamide |
| D-AlaNH2 | D-Alanylamide |
| N-Ac-Ala | N-Acetyl-L-alanyl |
| N-Ac-D-Ala | N-Acetyl-D-alanyl |
| Adala | L-Adamantylalanyl |
| | (I.e. L-2-Amino-3-adamant-1-ylpropionyl) |
| D-Adala | D-Adamantylalanyl |
| | (I.e. D-2-Amino-3-adamant-1-ylpropionyl) |
| N-Ac-Adala | N-Acetyl-L-adamantylalanyl |
| N-Ac-D-Adala | N-Acetyl-D-adamantylalanyl |
| 2-Bal | L-3-(Benzo[b]thien-2-yl)alanyl |
| 3-Bal | L-3-(Benzo[b]thien-3-yl)alanyl |
| D-2-Bal | D-3-(Benzo[b]thien-2-yl)alanyl |
| D-3-Bal | D-3-(Benzo[b]thien-3-yl)alanyl |
| NAc-2-Bal | N-Acetyl-L-3-(Benzo[b]thien-2-yl)alanyl |
| NAc-3-Bal | N-Acetyl-L-3-(Benzo[b]thien-3-yl)alanyl |
| NAc-D-2-Bal | N-Acetyl-D-3-(Benzo[b]thien-2-yl)alanyl |
| NAc-D-3-Bal | N-Acetyl-D-3-(Benzo[b]thien-3-yl)alanyl |
| Cha | L-Cyclohexylalanyl |
| N-Ac-Cha | N-Acetyl-L-Cyclohexylalanyl |
| D-Cha | D-Cyclohexylalanyl |
| N-Ac-D-Cha | N-Acetyl-D-cyclohexylalanyl |
| 1-Nal | L-3-(Naphth-1-yl)alanyl |
| 2-Nal | L-3-(Naphth-2-yl)alanyl |
| D-1-Nal | D-3-(Naphth-1-yl)alanyl |
| D-2-Nal | D-3-(Naphth-2-yl)alanyl |
| N-Ac-1-Nal | N-Acetyl-L-3-(Naphth-1-yl)alanyl |
| N-Ac-2-Nal | N-Acetyl-L-3-(Naphth-2-yl)alanyl |
| N-Ac-D-1-Nal | N-Acetyl-D-3-(Naphth-1-yl)alanyl |
| N-Ac-D-2-Nal | N-Acetyl-D-3-(Naphth-2-yl)alanyl |
| Aza-1-Nal | Aza-3-(Naphth-1-yl)alanyl |
| Aza-2-Nal | Aza-3-(Naphth-2-yl)alanyl |
| N-Ac-aza-1-Nal | N-Acetyl-aza-3-(Naphth-1-yl)alanyl |
| N-Ac-aza-2-Nal | N-Acetyl-aza-3-(Naphth-2-yl)alanyl |
| 2-Pal | L-3-(Pyrid-2-yl)alanyl |
| 3-Pal | L-3-(Pyrid-3-yl)alanyl |
| 4-Pal | L-3-(Pyrid-4-yl)alanyl |
| D-2-Pal | D-3-(Pyrid-2-yl)alanyl |
| D-3-Pal | D-3-(Pyrid-3-yl)alanyl |
| D-4-Pal | D-3-(Pyrid-4-yl)alanyl |
| N-Ac-2-Pal | N-Acetyl-L-3-(Pyrid-2-yl)alanyl |
| N-Ac-3-Pal | N-Acetyl-L-3-(Pyrid-3-yl)alanyl |
| N-Ac-4-Pal | N-Acetyl-L-3-(Pyrid-4-yl)alanyl |
| N-Ac-D-2-Pal | N-Acetyl-D-3-(Pyrid-2-yl)alanyl |
| N-Ac-D-3-Pal | N-Acetyl-D-3-(Pyrid-3-yl)alanyl |
| N-Ac-D-4-Pal | N-Acetyl-D-3-(Pyrid-4-yl)alanyl |
| 2-Qual | L-3-(Quinolin-2-yl)alanyl |
| 3-Qual | L-3-(Quinolin-3-yl)alanyl |
| 4-Qual | L-3-(Quinolin-4-yl)alanyl |
| D-2-Qual | D-3-(Quinolin-2-yl)alanyl |
| D-3-Qual | D-3-(Quinolin-3-yl)alanyl |
| D-4-Qual | D-3-(Quinolin-4-yl)alanyl |
| N-Ac-2-Qual | N-Acetyl-L-3-(Quinolin-2-yl)alanyl |
| N-Ac-3-Qual | N-Acetyl-L-3-(Quinolin-3-yl)alanyl |
| N-Ac-4-Qual | N-Acetyl-L-3-(Quinolin-4-yl)alanyl |
| N-Ac-D-2-Qual | N-Acetyl-D-3-(Quinolin-2-yl)alanyl |
| N-Ac-D-3-Qual | N-Acetyl-D-3-(Quinolin-3-yl)alanyl |
| N-Ac-D-4-Qual | N-Acetyl-D-3-(Quinolin-4-yl)alanyl |
| D-Thia or D-Thial | D-3-Thien-2-yl)alanyl |
| D-Thiaz | D-3-(Thiazol-4-yl)alanyl |
| D-4N(Nic)Cha | D-[4-(aminonicotinyl)cyclohexyl]alanyl |
| D-4N(Guan)Cha | D-[4-(guanido)cyclohexylalanyl |
| | Arginyl & Derivatives |
| Arg | L-Arginyl |
| D-Arg | D-Arginyl |
| HArg | L-Homoarginyl |
| | (I.e. L-2-Amino-6-guanidinohexanoyl) |
| D-Harg | D-Homoarginyl |
| | (I.e. D-2-Amino-6-guanidinohexanoyl) |

TABLE 1-continued

Amino Acyl Residue Abbreviations

| Abbreviation | Definition |
|---|---|
| Harg(Et) | L-2-Amino-6-$N^G$-ethylguanidinohexanoyl) |
| Harg(Et2) or | L-2-Amino-6-$N^G$-diethylguanidino- |
| Harg(Diethyl) | hexanoyl |
| NMeHarg | N-Methyl-L-homoarginyl |
| | Glycyl & Derivatives |
| Gly | Glycyl |
| N-Ac-Gly | N-Acetylglycyl |
| AzaGlyz | Azaglycyl |
| N-Ac-azaGly | N-Acetylazaglycyl |
| cprgly | 1-Amino-1-cyclopropanecarbonyl |
| t-Bugly | alpha-butyl-glycinyl |
| Abu | alpha-amino-butyric acid |
| | Leucyl, Isoleucyl & Derivatives |
| Ileu | L-Isoleucyl |
| D-Ileu | D-Isoleucyl |
| Leu | L-Leucyl |
| D-Leu | D-Leucyl |
| | Lysyl & Derivatives |
| Lys | L-Lysyl |
| D-Lys | D-Lysyl |
| Lys(GlyNic) | L-(N'-epsilon-glycylnicotinoyl)lysyl |
| D-Lys(GlyNic) | D-(N'-epsilon-glycylnicotinoyl)lysyl |
| Lys(AzaglyNic) | L-(N'-epsilon-azaglycylnicotinoyl)lysyl |
| D-Lys(AzaglyNic) | D-(N'-epsilon-azaglycylnicotinoyl)lysyl |
| Lys(Azagly-2-Fur) | L-(N'-epsilon-azaglycylfur-2-oyl)lysyl |
| D-Lys(Azagly-2-Fur) | D-(N'-epsilon-azaglycylfur-2-oyl)lysyl |
| Lys(Isp) or Lys(Nisp) | L-(N'-epsilon-isopropyl)lysyl |
| D-Lys(Isp) or D-Lys(Nisp) | D-(N'-epsilon-isopropyl)lysyl |
| D-Lys(MePip)CO | D-(N'-epsilon-(N"-methyl-N-piperidinyl)carbonyl)lysyl |
| D-Lys(Morph)CO | D-(N'-epsilon-(N"-Morpholino)carbonyl)lysyl |
| Lys(Nic) | L-(N'-epsilon-Nicotinyl)lysyl |
| D-Lys(Nic) | D-(N'-epsilon-Nicotinyl)lysyl |
| Lys(Pic) | L-(N'-epsilon-Picolyl)lysyl |
| Lys(Atz) | N-epsilon-(3-amino-1,2,4-triazol-5-yl)-L-lysyl |
| D-Lys(Atz) | N-epsilon-(3-amino-1,2,4-triazol-5-yl)-D-lysyl |
| D-Lys(Pic) | D-(N'-epsilon-Picolyl)lysyl |
| D-Lys(Pyz) | D-(N'-epsilon-(Pyrazin-2-yl)carbonyl)lysyl |
| Lys(2furfur) | L-(N'-epsilon-furfuryl)lysyl |
| DLys(AzaglyThiofur) | L-(N'-epsilon-Azaglycyl-2-thiophenecarbonyl)lysyl |
| | L-(N'-epsilon-Cyclohexyl)Lysyl |
| Lys(chex) | N-Methyl-(N'-epsilon-nicotinyl)lysyl |
| NMeLys(Nic) | D-(N'-epsilon-Azaglycyl-shikimyl) |
| DLys(AzaglyShik) | |
| DLys(BalaNic) | D-(N'-epsilon-beta-alanyl-nicotinyl)lysyl |
| DLys(Azagly4HFur) | D-(N'-epsilon-Azaglycyl-2-tetrahydrofuroyl)lysyl |
| DLys(Azagly3OHNaph) | D-(N'-epsilon-Azaglycyl-2-Hydroxy-Naphthyl-3-carbonyl)lysyl |
| Lys(OHIsp) | L-(N'-epsilon-1'-hydroxyisopropyl)lysyl |
| Lys(1,3OHIsp) | L-(N'-epsilon-1,3-dihydroxyisopropyl)lysyl |
| DLys(GlySalicyl) | D-(N'-epsilon-Azaglycyl-salicyl) |
| DLys(Azaglyacindole) | D-N'-epsilon-Azaglycyl-3-indoleacetyl) |
| DLys(FurEtamCO) | D-[N'-epsilon-(N"-carbonyldiaminoethane-N'"-2-furoyl)]lysyl |
| DLys(NicPropAmCO) | D-[N'-epsilon-(N"-carbonyldiaminopropane-N'"-nicotinyl)]lysyl |
| | Miscellaneous |
| Aca | N'-epsilon-Aminocaproyl (I.e. 6-Aminohexanoyl) |
| Aha | 7-Aminoheptanoyl |
| Ava | N'-delta-Aminovaleric acid (I.e. 5-Aminopentanoyl) |
| Dap | 2,3-Diaminopropionyl) |
| Sar | Sarcosyl (I.e. N-Methylglycol) |
| NAcSar | N-Acetyl-sarcosyl |
| N-Formyl-Sar | N-Formyl-sarcosyl |
| Nip | Nipecotyl |
| Inip | Isonipecotyl |

TABLE 1-continued

Amino Acyl Residue Abbreviations

| Abbreviation | Definition |
|---|---|
| | Ornithyl & Derivatives |
| Orn | Ornithyl |
| | (I.e. α,δ-Diaminovaleryl) |
| D-Orn | D-Ornithyl |
| Cit | Citrullyl |
| | (I.e. N'-delta-Aminocarbonyl-L-ornithyl) |
| D-Cit | D-Citrullyl |
| Hcit | Homocitrullyl |
| | (I.e. L-2-Amino-(6-aminocarbonylamino)hexanoyl |
| D-HCit | D-Homocitrullyl |
| | Phenylalanyl & Derivatives |
| Phe | L-Pheylalanyl |
| D-Phe | D-Phenylalanyl |
| 4-Br-Phe | L-3-(4-Bromophenyl)alanyl |
| D-4-Br-Phe | D-3-(4-Bromophenyl)alanyl |
| 4-Cl-Phe | L-3-(4-Chlorophenyl)alanyl |
| D-4-Cl-Phe | D-3-(4-Chlorophenyl)alanyl |
| 2,4-Cl-Phe | L-3-(2,4-Dichlorophenyl)alanyl) |
| D-2,4-Cl-Phe | D-3-(2,4-Dichlorophenyl)alanyl) |
| Aza-4-Cl-Phe | Aza-3-(4-chlorophenyl)alanyl |
| 4-F-Phe | L-3-(4-Fluorophenyl)alanyl |
| D-4-F-Phe | D-3-(4-Fluorophenyl)alanyl |
| Aza-4-F-Phe | Aza-3-(4-fluorophenyl)alanyl |
| 4-$CF_3$-Phe | L-3-(4-Trifluoromethylphenyl)alanyl |
| D-4-$CF_3$-Phe | D-3-(4-Trifluoromethylphenyl)alanyl |
| 4-$NO_2$-Phe | L-3-(4-Nitrophenyl)alanyl |
| D-4-$NO^2$-Phe | D-3-(4-Nitrophenyl)alanyl |
| N-Ac-Phe | N-Acetyl-L-phenylalanyl |
| N-Ac-D-Phe | N-Acetyl-D-phenylalanyl |
| N-Ac-4-Br-Phe | N-Acetyl-L-3-(4-Bromophenyl)alanyl |
| N-Ac-D-4-Br-Phe | N-Acetyl-D-3-(4-Bromophenyl)alanyl |
| N-Ac-4-Cl-Phe | N-Acetyl-L-3-(4-Chlorophenyl)alanyl |
| N-Ac-D-4-Cl-Phe | N-Acetyl-D-3-(4-Chlorophenyl)alanyl |
| N-Ac-4-F-Phe | N-Acetyl-L-3-(4-Fluorophenyl)alanyl |
| N-Ac-D-4-Phe | N-Acetyl-D-3-(4-Fluorophenyl)alanyl |
| N-Ac-4-$CF_3$-Phe | N-Acetyl-L-3-(4-Trifluoromethylphenyl)alanyl |
| N-Ac-D-4-$CF_3$-Phe | N-Acetyl-D-3-(4-trifluoromethylphenyl)alanyl |
| N-Ac-4-$NO_2$-Phe | N-Acetyl-L-3-(4-nitrophenyl)alanyl |
| N-Ac-D-4-$NO_2$-Phe | N-Acetyl-D-3-(4-nitrophenyl)alanyl |
| NMe(Isp)Phe | N-Methyl-3-|94-Isopropylamino)]phenyl]alanyl |
| Phe(Atz) | 3-(4-(3-amino-1,2,4-triazol-5-yl)phenyl)alanyl |
| NMePhe(Atz) | N-Methyl-[4-[5'-(3'-amino-1H-1',2',4'-triazolyl)phenyl])alanyl |
| | Prolyl & Derivatives |
| Pro | L-Prolyl |
| D-Pro | D-Prolyl |
| Pro(OH) | L-4-Hydroxyproline |
| D-Pro(OH) | D-4-Hydroxyproline |
| DePro or $\Delta^{3,4}$-Pro | 3,4-Didehydro-L-prolyl |
| N-Ac-DePro or N-Ac-$\Delta^{3,4}$-Pro | N-Acetyl-3,4-didehydro-L-proline |
| Thiopro | (R)-Thiazolidine-4-carbonyl |
| Aze | (S)-2-Azetidinecarbonyl |
| | Seryl & Derivatives |
| Ser | L-Seryl |
| D-Ser | D-Seryl |
| Hser | L-Homoseryl |
| NMeHser | N-Methyl-Homoseryl |
| | Tyrptophyl & Derivatives |
| Trp | L-Tryptyl |
| D-Trp | D-Tryptyl |
| Trp(Me) | L-(N-indole-methyl)Tryptyl |
| | L-(N-indole-methyl)Tryptyl |
| Tyr | L-Tyrosyl |
| N-Ac-Tyr | N-Acetyl-L-tyrosyl |
| D-Tyr | D-Tyrosyl |
| N-Ac-D-Tyr | N-Acetyl-D-tyrosyl |
| N-Ac-Tyr(OMe) | N-Acetyl-O-methyl-L-tyrosyl |

TABLE 1-continued

Amino Acyl Residue Abbreviations

| Abbreviation | Definition |
| --- | --- |
| N-Ac-D-Tyr(OMe) | N-Acetyl-O-methyl-D-tyrosyl |
| N-Me-Tyr | N-α-Methyl-L-tyrosyl |
| N-Me-D-Tyr | N-α-Methyl-D-tyrosyl |
| Tyr(OBz) | O-Benzyl-L-tyrosyl |
| Tyr(OMe) | O-Methyl-L-tyrosyl |
| D-Tyr(OBz) | O-Benzyl-D-tyrosyl |
| D-Tyr(OMe) | O-Methyl-D-tyrosyl |

In reference to the side-chain group "X" in compounds of this invention, when the term "Ω-amino-functional side chain" is used, what is meant is a terminally-amino-functionalized alkyl group such as 2-aminoethyl, 3-aminopropyl, 4-aminobutyl, and the like or a 4-aminocyclohexylmethyl group.

LHRH Antagonist Activity

Representative compounds of the present invention were evaluated in in vitro tests for receptor binding (pKI) and for LHRH antagonist potency ($pA_2$). The tests employed the methods detailed in F. Haviv, et al., *J. Med. Chem.*, 32: 2340–2344 (1989). The receptor binding affinities ($pK_I$) are the negative logarithms of the equilibtirum dissociation constants ($pA_2$) are the negative logarithms of the concentration of antagonist which shift the response curve roduced by the agonist leuprolide to two-fold higher concentration. (Leuprolide is the LHRH agonist having the structure 5-oxo-Pro$^1$-His$^2$-Trp$^3$-Ser$^4$-Tyr$^5$-D-Leu$^6$-Leu$^7$-Arg$^8$-Pro$^9$-NHEt and is disclosed and claimed in U.S. Pat. No. 4,005,063.) Typically $pA_2$ values of 9.5 or greater are indicative of good LHRH antagonist potency.

The results of these test for representative compounds in accordance with this invention are presented in Table 2.

TABLE 2

| Example | $pA_2$ |
| --- | --- |
| 1 | 11.45 |
| 2 | 11.85 |
| 3 | 11.31 |
| 4a | 11.25 |
| 4b | 10.63 |
| 4c | 10.80 |
| 4d | 10.86 |
| 4e | 10.47 |
| 5a | 10.72 |
| 5b | 11.53 |
| 5c | 10.88 |
| 5d | 10.26 |
| 5e | 10.17 |
| 6a | 10.80 |
| 6b | 10.62 |
| 7 | 11.05 |
| 8 | 11.1 |
| 9 | 11.05 |
| 10 | 11.30 |
| 11 | 10.77 |
| 12 | 10.70 |
| 13 | 11.10 |
| 14 | 9.78 |
| 15 | 11.55 |
| 16 | 11.1 |
| 17 | 11.14 |
| 18 | 11.51 |
| 19a | 10.62 |
| 19b | 11.18 |
| 19c | 11.48 |
| 23 | 11.12 |
| 25a | 10.44 |
| 25b | 10.39 |
| 36 | 10.97 |
| 37a | 10.78 |
| 37b | 11.25 |
| 38a | 10.55 |
| 38d | 10.7 |
| 38e | 10.36 |
| 38f | 10.67 |
| 42 | 10.59 |
| 43 | 11.07 |
| 45 | 11.38 |
| 46 | 10.96 |
| 48a | 11.10 |
| 48b | 10.43 |
| 48c | 10.54 |
| 48d | 10.90 |
| 48f | 10.9 |
| 48g | 10.9 |
| 48h | 10.42 |
| 48i | 10.44 |
| 48j | 10.77 |
| 48k | 10.77 |
| 49a | 10.81 |
| 49b | 10.81 |
| 49c | 10.37 |
| 49d | 11.78 |
| 50d | 10.32 |
| 50e | 10.54 |
| 50g | 10.9 |
| 51a | 10.96 |
| 51d | 10.85 |
| 51e | 11.16 |
| 51f | 10.82 |
| 52 | 10.81 |
| 53a | 10.48 |
| 54 | 10.52 |
| 57a | 10.84 |
| 57b | 10.05 |
| 57c | 10.73 |
| 57d | 11.43 |
| 57e | 10.92 |
| 58 | 10.59 |
| 59 | 10.44 |
| 60 | 10.55 |
| 62 | 10.58 |
| 63 | 11.35 |
| 64 | 10.94 |
| 65a | 10.6 |
| 65b | 11.64 |
| 65c | 10.54 |

Effect and Utilities of LHRH Agonists and Antagonists

The LHRH agonist and antagonist compounds of the invention are useful for treatment of precocious puberty, prostate cancer, benign prostatic hyperplasia (BPH), endometriosis, uterine fibroids, breast cancer, acne, premenstrual syndrome, polycystic ovary syndrome and diseases which result from excesses or deficiencies in gonadal hormone production in either sex of humans and animals. The LHRH antagonists of the invention are also useful for controlling reproduction in both females and males. Compounds of the invention are useful for suppressing levels of dihydrotestosterone (DHT).

In the practice of the method of this invention an effective amount of a compound of the invention or a pharmaceutical composition containing the same is administered to the human or animal in need of, or desiring, such treatment. These compounds or compositions may be administered by any of a variety of routes depending upon the specific end use, including orally, parenterally (including subcutaneous, intramuscular and intraveneous administration), vaginally (particularly for contraception), rectally, buccally (including sublingually), transdermally or intranasally. The most suitable mute in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administratiom may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

Synthesis of the Peptides of this Invention

The polypeptides of the present invention may be synthesized by techniques known to those skilled in the art as, for example, by so-called "solid phase" peptide synthesis or by usual methods of solution phase chemistry. A summary of available solid phase peptide synthetic techniques may be found in J. M. Stewart and J. D. Young, Solid Phase Peptide Synthesis, W. H. Freeman Co., San Francisco, 1963 and J. Meienhofer, Hormonal Proteins and Peptides, Vol. 2., p.46, Academic Press (New York), 1973. For classical solution synthesis see G. Schroder and K. Lupke, The Peptides, vol. 1, Academic Pres (New York), 1965.

In general, these methods comprise the sequential addition of one or more amino acids or suitably protected amino acids to a growing peptide chain bound to a suitable resin. The starting amino acids are commercially available or, where novel in the compounds of this invention, are synthesized by methods detailed below from readily available starting materials.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis. In this method of preparing compounds of the invention, the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (BOC), benzyloxycarbonyl (Cbz), biphenylisopropyloxycarbonyl, t-amyloxycarbonyl, isobomyloxycarbonyl, (alpha, alpha)-dimethyl-3, 5dimethoxybenzyloxycarbonyl, o-nitrophenylsulfenyl, 2-cyano-t-butyloxycarbonyl, 9-fluorenylmethyloxycarbonyl and the like. The t-butyloxycarbonyl ("BOC" or "t-BOC") protecting group is preferred.

Particularly preferred side chain protecting groups are, for side-chain amino groups as in lysine and arginine: nitro, p-toluene-sulfonyl, 4-methoxybenzenesulfonyl, Cbz, BOC and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tertahydropyranyl; for histidine: benzyl, Cbz, p-toluenesulfonyl and 2,4-dinitrophenyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylamino-polystyrene-divinylbenzene polymer described by P. Rivaille, et al, *Helv. Chim. Acta.,* 54, 2772 (1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha-N-BOC amino acid cesium salt with the resin in DMF at about 50° C. for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C, most preferably 25° C. in a solvent such as dichloromethane or DMF, preferably dichloromethane. The coupling of the carboxyl group to the N-methyl-Ser(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

Following complete synthesis of the desired peptide chain, it is treated with a 30% solution of piperidine in dimethylformamide to remove the FMOC protecting group on the 6-postion $\Omega$-amino-functionalized residue. This material is washed several times, typically with methylene chloride. The free amine functionality of the 6-position is then coupled with an aminoacyl residue using the coupling technique described above. Following deblocking of this derivatized protected 6-position residue by methods described above, the free amine functionality of this side-chain can be further derivatized by coupling and deblocking, if desired.

Upon completion of the entire reaction sequence, the resin-bound peptide is cleaved from the solid support. With benzyhydrlamine resin, this can be done by treatment with dry HF in the presence of anisole at 0° C., with Merrifield resin it can be done by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 48 hours preferably about 18 hours. Alternatively, the peptide may be removed from the resin by transesterification, e.g., with methanol, followed by aminolysis or by direct transamidation. The final product is lyophilized and then purified by HPLC methods known in the art.

These general synthetic methods are exemplified by the following Examples and, in particular, Example 1 which gives the order, number, and duration of coupling steps to prepare NAc-D2Nal$^1$-D4ClPhe$^2$-D3Pal$^3$-Ser$^4$-NMeTyr$^5$-DLys(N-epsilon-Gly-Nicotinyl)$^6$-Leu$^7$-Lys(N-epsilon-Isopropyl)$^8$-Pro$^9$-DAla$^{10}$NH$_2$.

EXAMPLE 1

Preparation of NAc-D2Nal$^1$-D4ClPhe$^2$-D3Pal$^3$-Ser$^4$-NMeTyr$^5$-DLys(N-epsilon-Gly-Nicotinyl)$^6$-Leu$^7$-Lys(N-epsilon-Isopropyl)$^8$-Pro$^9$-DAla$^{10}$NH$_2$ In the reaction vessel of a Milligen-Biosearch 9500 peptide synthesizer was placed 1 g (0.6 mmol) of D-Ala-NH-resin (4-methyl-benzhydrylamine resin). Amino acids were added sequentially according to the following synthetic cycle:

1. Deblocking, to remove the t-BOC group from the alpha-amino function of the peptide, was carried out using a solution of 45% trifluoroacetic acid (TFA), 2.5% anisole, 2.0% dimethyl phosphite, and 50.5% methylene chloride. The resin was prewashed with the deblocking solution for one minute and then the deblocking reaction is run for 20 minutes.
2. Base wash, to remove and neutralize the TFA used for deprotection, was carried out using a solution of 10% N,N'-diisopropylethylamine in methylene chloride. The resin was washed with base three times for one minute each time after a deblocking step.
3. Coupling reaction was carried out using a 3-fold molar excess of 0.3M DMF solution of a t-BOC protected amino acid derivative along with a 3-fold molar excess of 0.3M methylene chloride solution of diisopropylcarbodiimide as activator. The activated amino acid is then coupled to the free alpha amino group of the peptide-resin. The reaction time is as described in the synthesis protocol.
4. Wash, each reaction step was followed by three washes of one minute each: one of methylene chloride, one of (1:1) methylene chloride/DMF, and one of DMF.

Synthesis Protocol:
The amino protected amino acids were coupled to the resin according the following order, number, and duration of couplings:

Amino Acid Coupling
1. B OC-Pro two-1 h
2. BOC-Lys(N-epsilon-Cbz,Isopropyl) two-1 h
3. BOC-Leu two-1 h
4. BOC-D-Lys(N-epsilon-FMOC) two-1 h
5. BOC-NMe-Tyr(O-2,6-diCl-Bzl) two-1 h
6. BOC-Ser(OBzl) two-1 h
7. BOC-D-3Pal two-6 h
8. BOC-D-4ClPhe two-2 h
9. BOC-D2Nal two-2 h
0 10. Acetic acid two-2 h Upon completion of the synthesis the resin was treated with 30% piperidine in DMF solution for 4 to 24 h to remove the FMOC protecting group. After several washes with methylene chloride the peptide-resin is coupled first with BOC-Gly and then with nicotinic acid using the two-2 h protocol. The peptide-resin was then dried overnight over P$_2$O$_5$ under vacuum and then treated with dry HF in the presence of anisole at 0° C. for 1 h to cleave the peptide from the resin. The excess of reagent was removed in vacuo. The resin was washed first with ether, then stirred at room temperature with a solution of (1:1:0.1) water/acetonitrile/acetic acid (50 ml) for 15 minutes, and filtered. The filtrate was lyophilized to give the crude peptide as a fluffy powder. This was purified by HPLC using a (25×2.5 cm) Dynamax C-18 column (8 micron) with solvent mixtures varying in a gradient ranging from 89% H$_2$O/11% CH$_3$CN/0.1% TFA over a period of 20 minutes. The UV detector was set at 260 nM. The product is eluted at 14.7 min as a single peak, collected and lyophilized to give pure NAc-D2Nal-D4ClPhe-D3Pal-Ser-NMeTyr-DLys(N-epsilon-Gly-Nicotinyl)-Leu-Lys(N-epsilon-Isopropyl)-Pro-DAlaNH$_2$ as the trifluoroacetate salt. FAB Mass spec. m/e 1591 (M+H)$^+$. Amino Acid Anal: 1.00 Ala; 1.01 Pro; 1.57 Lys; 0.99 Leu; 1.01 NMeTyr; 0.47 Ser.

EXAMPLE 2

NAc-D2Nal$^1$-D4ClPhe$^2$-D3Pal$^3$-Ser$^4$-NMeTyr$^5$-DLys(N-epsilon-Azagly-2-Furoyl)$^6$-Leu$^7$-Lys(N-epsilon-Isopropyl)$^8$-Pro$^9$-DAla$^{10}$NH$_2$ The same procedure described in Example 1 was used to remove of the FMOC group. Instead of coupling with BOC-Gly the peptide is treated with a solution of carbonyldiimidazole (0.9 g) in DMF (18 ml) for 15 minutes, washed (×3) with methylene chloride, and then reacted overnight with a solution of 2-furoic hydrazide (0.53 g) in DMF (18 ml). The resin was washed (×3) with methylene chloride, dried overnight over P$_2$O$_5$, and treated with dry HF/anisole at 0° C. for 1 h. After work-up, lyophilization, and HPLC purification NAc-D2Nal-D4ClPhe-D3Pal-Ser-NMeTyr-DLys(N-epsilon-Azagly-2-Furoyl)-Leu-Lys(N-epsilon-Isopropyl)-Pro-DAlaNH$_2$ was obtained as the trifluoroacetate salt; R$_t$=25.7 min; FAB Mass spec. m/e 1581 (M+H)$^+$. Amino Acid Analysis: 0.98 Ala; 1.02 Pro; 1.58 Lys; 1.00 Leu; 1.12 NMeTyr; 0.52 Ser.

EXAMPLE 3

NAc-D2Nal$^1$-D4ClPhe$^2$-D3Pal$^3$-Ser$^4$-NMeTyr$^5$-DLys(N-epsilon-Azagly-Nicotinyl)$^6$-Leu$^7$-Lys(N-epsilon-Isopropyl)$^8$-Pro$^9$-DAla$^{10}$NH$_2$ The same procedure described in Example 2 was used but substituting 2-furoic hydrazide with nicotinic hydrazide (0.575 g). After work-up, lyophilization, and HPLC purification NAc-D2Nal-D4ClPhe-D3Pal-Ser-NMeTyr-DLys(N-epsilon-Azagly-3-Nicotinyl)-Leu-Lys(N-epsilon-Isopropyl)-Pro-DAlaNH$_2$ was obtained as the trifluoroacetate salt; R$_t$=16.0 min; FAB Mass spec. m/e 1592 (M+H)$^+$. Amino Acid Analysis: 1.02 Ala; 1.01 Pro; 1.61 Lys; 0.99 Leu; 1.12 NMeTyr; 0.48 Ser.

EXAMPLE 4

Using the procedure described in Example 1 but substituting BOC-Gly with the appropriate protected amino acid the following compounds were obtained:

(a) NAc-D2Nal$^1$-D4ClPhe$^2$-D3Pal$^3$-Ser$^4$-NMeTyr$^5$-DLys(N-epsilon-beta-Alanyl)-Nicotinyl)$^6$-Leu$^7$-Lys(N-epsilon-Isopropyl)$^8$-Pro$^9$-DAla$^{10}$NH$_2$ as the trifluoroacetate salt; R$_t$=16.50 min; FAB Mass spec. m/e 1605 (M+H)$^+$. Amino Acid Analysis: 1.01 Ala; 1.01 Pro; 0.85 Lys(Isp); 1.02 Leu; 0.96 Lys;1.07 NMeTyr; 0.41 Ser; 0.71 3Pal; 0.75 4ClPhe.

(b) NAc-D2Nal$^1$-D4ClPhe$^2$-D3Pal$^3$-Ser$^4$-NMeTyr$^5$-DLys[N-epsilon-(gamma-Aminobutyryl)Nicotinyl]$^6$-Leu$^7$-Lys(N-epsilon-Isopropyl)$^8$-Pro$^9$-DAla$^{10}$NH$_2$ as the trifluoroacetate salt; R$_t$=31.50 min; FAB Mass spec. m/e 1619 (M+H)$^+$. Amino Acid Analysis: 0.98 Ala; 0.90 Lys(Isp); 1.05 Pro; 1.04 Leu; 0.92 Lys; 0.97 NMeTyr; 0.49 Ser; 1.05 3Pal; 1.1 4ClPhe.

(c) NAc-D2Nal$^1$-D4ClPhe$^2$-D3Pal$^3$-Ser$^4$-NMeTyr$^5$-DLys[N-epsilon-DSer-Nicotinyl]$^6$-Leu$^7$-Lys(N-epsilon-Isopropyl)$^8$-Pro$^9$-DAla$^{10}$NH$_2$ as the trifluoroacetate salt; R$_t$=31.50 min; FAB Mass spec. m/e 1621 (M+H)$^+$. Amino Acid Analysis: 0.99 Ala; 1.02 Pro; 0.92 Lys(Isp); 1.01 Leu; 0.97 Lys; 1.03 NMeTyr; 1.06 Ser; 1.13 3Pal; 1.23 4ClPhe.(d) NAc-D2Nal$^1$-D4ClPhe$^2$-D3Pal$^3$-Ser$^4$-NMeTyr$^5$-DLys(N-epsilon-Sar-Nicotinyl)$^6$-Leu$^7$-Lys(N-epsilon-Isopropyl)$^8$-Pro$^9$-DAla$^{10}$NH$_2$ as the trifluoroacetate salt; R$_t$=20.84 min; FAB Mass spec. m/e 1605

(M+H)+. Amino Acid Analysis: 0.99 Ala; 1.04 Pro; 0.93 Lys(Isp); 1.01 Leu; 0.96 Lys; 1.06 Sar; 0.94 NMeTyr; 0.47 Ser; 1.01 3Pal; 1.05 4ClPhe.

(e) NAc-D2Nal$^1$-D4ClPhe$^2$-D3Pal$^3$-Ser$^4$-NMeTyr$^5$-DLys [N-epsilon-(N-epsilon-aminocaproyl)-Nicotinyl]$^6$-Leu$^7$-Lys(N-epsilon-Isopropyl)$^8$-Pro$^9$-DAla$^{10}$NH$_2$ as the trifluoroacetate salt; $R_t$=17.84 min; FAB Mass spec. m/e 1647 (M+H)+. Amino Acid Analysis: 1.02 Ala; 1.00 Pro; 093 Lys (Isp); 1.01 Leu; 0.97 Lys; 1.11 NMeTyr; 0.49 Ser; 1.13 3Pal; 1.10 4ClPhe.

EXAMPLE 5

Using the procedure described in Example 2 but substituting furoic hydrazide with the appropriate acid hydrazides the following compounds were obtained:

(a) NAc-D2Nal$^1$-D4ClPhe$^2$-D3Pal$^3$-Ser$^4$-NMeTyr$^5$-DLys (N-epsilon-Azagly-2-Tetrahydrofuroyl)$^6$-Leu$^7$-Lys(N-epsilon-Isopropyl)$^8$-Pro$^9$-DAla$^{10}$NH$_2$ is obtained as the trifluoroacetate salt; $R_t$=17.92 min; FAB Mass spec. m/e 1585 (M+H)+. Amino Acid Analysis: 1.00 Ala; 1.05 Pro; 0.94 Lys; 1.01 Leu; 0.97 NMeTyr; 0.48 Ser; 1.03 3Pal; 1.07 4ClPhe.

(b) NAc-D2Nal$^1$-D4ClPhe$^2$-D3Pal$^3$-Ser$^4$-NMeTyr$^5$-DLys (N-epsilon-Azagly-2-Thienylcarbonyl)$^6$-Leu$^7$-Lys(N-epsilon-Isopropyl)$^8$-Pro$^9$-DAla$^{10}$NH$_2$ is obtained as the trifluoroacetate salt; $R_t$=18.8 min; FAB Mass spec. m/e 1597 (M+H)+. Amino Acid Analysis: 1.02 Ala; 1.01 Pro; 0.93 Lys(Isp); 1.01 Leu; 0.97 Lys; 1.02 NMeTyr; 0.51 Ser; 1.07 3Pal; 1.14 4ClPhe.

(c) NAc-D2Nal$^1$-D4ClPhe$^2$-D3Pal$^3$-Ser$^4$-NMeTyr$^5$-DLys (N-epsilon-Azagly-Salicyl)$^6$-Leu$^7$-Lys(N-epsilon-Isopropyl)$^8$-Pro$^9$-DAla$^{10}$NH$_2$ was obtained as the trifluoroacetate salt; $R_t$=21.72 min; FAB Mass spec. m/e 1607 (M+H)+. Amino Acid Analysis: 1.03 Ala; 0.98 Pro; 0.95 Lys(Isp); 1.01 Leu 1.02 NMeTyr; 0.61 Ser; 1.08 3Pal; 1.05 4ClPhe.

(d) NAc-D2Nal$^1$-D4ClPhe$^2$-D3Pal$^3$-Ser$^4$-NMeTyr$^5$-DLys [N-epsilon-Azagly-(3-OH-2-Naphthoyl)]$^6$-Leu$^7$-Lys(N-epsilon-Isopropyl)$^8$-Pro$^9$-DAla$^{10}$NH$_2$ was obtained as the trifluoroacetate salt; $R_t$=24.16 min; FAB Mass spec. m/e 1657 (M+H)+. Amino Acid Analysis: 1.02 Ala; 1.00 Pro; 0.91 Lys(Isp); 1.02 Leu; 0.95 Lys; 1.1 NMeTyr; 0.51 Ser; 1.05 3Pal; 1.1 4ClPhe.

(e) NAc-D2Nal$^1$-D4ClPhe$^2$-D3Pal$^3$-Ser$^4$-NMeTyr$^5$-DLys (N-epsilon-Azagly-Isonicotinyl)$^6$-Leu$^7$-Lys(N-epsilon-Isopropyl)$^8$-Pro$^9$-DAla$^{10}$NH$_2$ was obtained as the trifluoroacetate salt; $R_t$=22.08 min; FAB Mass spec. m/e 1590 (M+H)+. Amino Acid Analysis: 1.01 Ala; 1.02 Pro; 0.96 Lys; 1.00 Leu; 0.82 NMeTyr; 0.50 Ser; 1.04 3Pal; 1.1 4ClPhe.

EXAMPLE 6

Using the procedure described in Example 1 but substituting nicotinic acid with the appropriate acids the following compounds are obtained:

(a) NAc-D2Nal$^1$-D4ClPhe$^2$-D3Pal$^3$-Ser$^4$-NMeTyr$^5$-DLys (N-epsilon-Gly-2-Furoyl)$^6$-Leu$^7$-Lys(N-epsilon-Isopropyl)$^8$-Pro$^9$-DAla$^{10}$NH$_2$ was obtained as the trifluoroacetate salt; $R_t$=17.78 min; FAB Mass spec. m/e 1580 (M+H)+. Amino Acid Analysis: 1.00 Ala; 1.01 Pro; 0.90 Lys(Isp); 0.99 Leu; 0.93 Lys; 0.82 NMeTyr; 0.48 Ser; 0.95 3Pal; 1.02 4ClPhe.

(b) NAc-D2Nal$^1$-D4ClPhe$^2$-D3Pal$^3$-Ser$^4$-NMeTyr$^5$-DLys (N-epsilon-Gly-Shikimyl)$^6$-Leu$^7$-Lys(N-epsilon-Isopropyl)$^8$-Pro$^9$-DAla$^{10}$NH$_2$ was obtained as the trifluoroacetate salt; $R_t$=31.5 min; FAB Mass spec. m/e 1642 (M+H)+. Amino Acid Analysis: 1.04 Ala; 1.06 Pro; 0.91 Lys(Isp); 1.03 Leu; 1.05 Lys; 1.08 NMeTyr; 0.47 Ser; 1.05 3Pal; 1.08 4ClPhe.

EXAMPLE 7

NAc-D2Nal$^1$-D4ClPhe$^2$-D3Pal$^3$-Ser$^4$-NMeTyr$^5$-DLys(N-epsilon-DSer-Nicotinyl)$^6$-Leu$^7$-Arg$^8$-Pro$^9$-DAla$^{10}$NH$_2$ Using the procedure described in Example 1, but substituting BOC-Arg(Tos) for BOC-Lys(N-epsilon-Cbz, Isopropyl) and BOC-D-Ser(OBzl) for t-BOC-Gly yields after work-up, lyophilization, and HPLC purification NAc-D2Nal-D4ClPhe-D3Pal-Ser-NMeTyr-DLys(N-epsilon-DSer-Nicotinyl)-Leu-Arg-Pro-DAlaNH$_2$ was obtained as the trifluoroacetate salt; $R_t$=33.5 min; FAB Mass spec. m/e 1607 (M+H)+. Amino Acid Analysis: 0.97 Ala; 1.02 Pro; 0.98 Arg; 1.02 Leu; 1.00 Lys; 1.13 NMeTyr; 0.96 Ser; 1.17 3Pal; 1.25 4ClPhe.

EXAMPLE 8

NAc-D2Nal$^1$-D4ClPhe$^2$-D3Pal$^3$-Ser$^4$-NMeTyr$^5$-DLys(N-epsilon-DSer-Acetyl)$^6$-Leu$^7$-Arg$^8$-Pro$^9$-DAla$^{10}$NH$_2$ Using the procedure described in Example 7, but substituting acetic acid for nicotinic acid, yields after work-up, lyophilization, and HPLC purification NAc-D2Nal-D4ClPhe-D3Pal-Ser-NMeTyr-DLys(N-epsilon-DSer-Acetyl)-Leu-Arg-Pro-DAlaNH$_2$ was obtained as the trifluoroacetate salt; $R_t$=52.5 min; FAB Mass spec. m/e 1544 (M+H)+. Amino Acid Analysis: 1.00 Ala; 1.01 Pro; 0.98 Arg; 1.02 Leu; 0.82 Lys; 0.95 NMeTyr; 1.08 Ser.

EXAMPLE 9

NAc-D2Nal$^1$-D4ClPhe$^2$-D3Pal$^3$-Ser$^4$-NMeTyr$^5$-DLys(N-epsilon-Ser-Acetyl)$^6$-Leu$^7$-Arg$^8$-Pro$^9$-DAla$^{10}$NH$_2$ Using the procedure described in Example 8 but substituting BOC-Ser(OBzl) for BOC-DSer(OBzl), after work-up, lyophilization, and HPLC purification NAc-D2Nal-D4ClPhe-D3Pal-Ser-NMeTyr-DLys(N-epsilon-Ser-Acetyl)-Leu-Arg-Pro-DAlaNH$_2$ was obtained as the trifluoroacetate salt; $R_t$=23.3 min; FAB Mass spec. m/e 1544 (M+H)+. Amino Acid Analysis: 1.01 Ala; 1.01 Pro; 0.98 Arg; 1.01 Leu; 0.70 Lys; 1.08 NMeTyr; 0.96 Ser.

EXAMPLE 10

NAc-D2Nal$^1$-D4ClPhe$^2$-D3Pal$^3$-Ser$^4$-NMeTyr$^5$-DLys(N-epsilon-Gly-Nicotinyl)$^6$-Leu$^7$-Arg$^8$-Pro$^9$-DAla$^{10}$NH$_2$ Using the procedure described in Example 1 but substituting BOC-Arg(Tos) for BOC-Lys(N-epsilon-Cbz, Isopropyl), after work-up, lyophilization, and HPLC purification NAc-D2Nal-D4ClPhe-D3Pal-Ser-NMeTyr-DLys(N-epsilon-Gly-Nic)-Leu-Arg-Pro-DAlaNH$_2$ is obtained as the trifluoroacetate salt; $R_t$=33.7 min; FAB Mass spec. m/e 1577 (M+H)+. Amino Acid Analysis: 0.99 Ala; 1.06 Pro; 1.00 Arg; 1.04 Leu; 0.98 Lys; 0.93 Gly; 0.96 NMeTyr; 0.48 Ser; 1.06 3Pal; 1.10 4ClPhe.

EXAMPLE 11

NAc-D2Nal$^1$-D4ClPhe$^2$-D3Pal$^3$-Ser$^4$-NMeTyr$^5$-DLys(N-epsilon-DSer-Shikimyl)$^6$-Leu$^7$-Arg$^8$-Pro$^9$-DAla$^{10}$NH$_2$ Using the procedure described in Example 7 but substituting shikimic acid for nicotinic acid, after work-up, lyophilization, and HPLC purification NAc-D2Nal-D4ClPhe-D3Pal-Ser-NMeTyr-DLys(N-epsilon-DSer-Shikimyl)-Leu-Arg-Pro-DAlaNH$_2$ is obtained as the trifluoroacetate salt; $R_t$=20.6 min; FAB Mass spec. m/e 1658

(M+H)$^+$. Amino Acid Analysis: 1.04 Ala; 0.97 Pro; 0.96 Arg; 1.02 Leu; 0.97 Lys; 0.98 NMeTyr; 0.96 Ser; 1.07 3Pal; 1.1 4ClPhe.

EXAMPLE 12

NAc-D2Nal$^1$-D4ClPhe$^2$-D3Pal$^3$-Ser$^4$-NMeTyr$^5$-DLys(N-epsilon-DSer-Acetyl)$^6$-Leu$^7$-Arg$^8$-Pro(4OH)$^9$-DAla$^{10}$NH$_2$ Using the procedure described in Example 8 but substituting BOC-Pro(4OH) for BOC-Pro, after work-up, lyophilization, and HPLC purification NAc-D2Nal-D4ClPhe-D3Pal-Ser-NMeTyr-DLys(N-epsilon-DSer-Acetyl)-Leu-Arg-Pro(4OH)-DAlaNH$_2$ was obtained as the trifluoroacetate salt; R$_t$=36.7 min; FAB Mass spec. m/e 1561 (M+H)$^+$. Amino Acid Analysis: 1.00 Ala; 0.98 Arg; 1.01 Leu; 0.97 Lys; 1.20 NMeTyr; 1.00 Ser; 1.16 3Pal; 1.22 4ClPhe.

EXAMPLE 13

NAc-D2Nal$^1$-D4ClPhe$^2$-D3Pal$^3$-Ser$^4$-NMeTyr$^5$-DLys(N-epsilon-DSer-Acetyl)$^6$-Leu$^7$-Harg$^8$-Pro$^9$-DAla$^{10}$NH$_2$ Using the procedure described in Example 8 but substituting BOC-Harg(Tos) for BOC-Arg(Tos), after work-up, lyophilization, and HPLC purification NAc-D2Nal-D4ClPhe-D3Pal-Ser-NMeTyr-DLys(N-epsilon-DSer-Acetyl]-Leu-Harg-Pro-DAlaNH$_2$ was obtained as the trifluoroacetate salt; R$_t$=22.5 min; FAB Mass spec. m/e 1558 (M+H)$^+$. Amino Acid Analysis: 1.00 Ala; 1.02 Pro; 0.99 Leu; 1.00 Lys; 0.92 NMeTyr; 1.03 Ser; 0.99 3Pal; 1.00 4ClPhe.

EXAMPLE 14

NAc-D2Nal$^1$-D4ClPhe$^2$-D3Pal$^3$-Ser$^4$-NMeTyr$^5$-DLys[N-epsilon-(N'-Carbonyl-Diaminoethane-N"-Nicotinyl)]$^6$-Leu$^7$-Arg$^8$-Pro$^9$-DAla$^{10}$NH$_2$ The procedure described in Example 7 was used up to the step of the removal of the FMOC group. Instead of coupling with BOC-Ser(OBzl) the peptide is treated with a solution of carbonyldiimidazole (0.6 g) in DMF (18 ml) for 20 minutes, washed (×3) with methylene chloride, and then reacted for 4 h with a solution of ethylenediamine (2ml) in (1:1) DMF/methylene chloride (20 ml). The resin is again washed (×3) with methylene chloride and coupled with nicotinic acid using the protocol described above. The peptide resin was then dried overnight over P$_2$O$_5$, and treated with HF/anisole at 0° C. for 1 h. After work-up, lyophilization, and HPLC purification NAc-D2Nal-D4ClPhe-D3Pal-Ser-NMeTyr-DLys[N-epsilon-(N'-Carbonyl-Diaminoethane-N"-Nicotinyl)]-Leu-Arg-Pro-DAlaNH$_2$ was obtained as the trifluoroacetate salt; R$_t$=20.6 min; FAB Mass spec. m/e 1606 (M+H)$^+$. Amino Acid Analysis: 1.04 Ala; 1.00 Pro; 0.97 Arg; 1.04 Leu; 0.92 Lys; 0.95 NMeTyr; 0.46 Ser; 1.04 3Pal; 1.1 4ClPhe.

EXAMPLE 15

NAc-D2Nal$^1$-D4ClPhe$^2$-D3Pal$^3$-Ser$^4$-NMeTyr$^5$-DLys[N-epsilon-(N'-Carbonyl-Diaminoethane-N"-Shikimyl)]$^6$-Leu$^7$-Arg$^8$-Pro$^9$-DAla$^{10}$NH$_2$ The same procedure described in Example 14 was used but substituting shikimic acid for nicotinic acid. After work-up, lyophilization, and HPLC purification NAc-D2Nal-D4ClPhe-D3Pal-Ser-NMeTyr-DLys[N-epsilon-(N'-Carbonyl-Diaminoethane-N"-Shikimyl)]-Leu-Arg-Pro-DAlaNH$_2$ was obtained as the trifluoroacetate salt; R$_t$=20.8 min; FAB Mass spec. m/e 1657 (M+H)$^+$. Amino Acid Analysis: 1.01 Ala; 0.98 Pro; 0.94 Arg; 1.02 Leu; 0.99 Lys; 0.85 NMeTyr; 0.48 Ser; 1.02 3Pal; 1.08 4ClPhe.

EXAMPLE 16

NAc-D2Nal$^1$-D4ClPhe$^2$-D3Pal$^3$-Ser$^4$-NMeTyr$^5$-DLys(N-epsilon-DSer-2-Furoyl)$^6$-Leu$^7$-Arg$^8$-Pro$^9$-DAla$^{10}$NH$_2$ Using the procedure described in Example 11 but substituting 2-furoic acid for shikimic acid, after work-up, lyophilization, and HPLC purification NAc-D2Nal-D4CLPhe-D3Pal-Ser-NMeTyr-DLys(N-epsilon-DSer-2-Furoyl)-Leu-Arg-Pro-DAlaNH$_2$ was obtained as the trifluoroacetate salt; R$_t$=23.2 min; FAB Mass spec. m/e 1595 (M+H)$^+$. Amino Acid Analysis: 1.03 Ala; 1.01 Pro; 1.03 Leu; 0.96 Lys; 1.03 NMeTyr; 0.88 Ser; 1.02 3Pal; 1.1 4ClPhe.

EXAMPLE 17

NAc-D2Nal$^1$-D4ClPhe$^2$-D3Pal$^3$-Ser$^4$-NMeTyr$^5$-DLys(N-epsilon-Gly-Shikimyl)$^6$-Leu$^7$-Arg$^8$-Pro$^9$-DAla$^{10}$NH$_2$ Using the procedure described in Example 10 but substituting shikimic acid for nicotinic acid, after work-up, lyophilization, and HPLC purification NAc-D2Nal-D4ClPhe-D3Pal-Ser-NMeTyr-DLys(N-epsilon-Gly-Shikimyl)-Leu-Arg-Pro-DAlaNH$_2$ was obtained as the trifluoroacetate salt; R$_t$=20.6 min; FAB Mass spec. m/e 1628 (M+H)$^+$. Amino Acid Analysis: 1.03 Ala; 1.01 Pro; 0.98 Arg; 1.04 Leu; 0.97 Lys; 1.1 NMeTyr; 0.41 Ser; 1.04 3Pal; 1.1 4ClPhe.

EXAMPLE 18

NAc-D2Nal$^1$-D4ClPhe$^2$-D3Pal$^3$-Ser$^4$-NMeTyr$^5$-DLys(N-epsilon-Gly-2Furoyl)$^6$-Leu$^7$-Arg$^8$-Pro$^9$-DAla$^{10}$NH$_2$ Using the procedure described in Example 17 but substituting 2-furoic acid for shikimic acid, after work-up, lyophilization, and HPLC purification NAc-D2Nal-D4ClPhe-D3Pal-Ser-NMeTyr-DLys(N-epsilon-Gly-2Furoyl)-Leu-Arg-Pro-DAlaNH$_2$ was obtained as the trifluoroacetate salt; R$_t$=23.8 min; FAB Mass spec. m/e 1566 (M+H)$^+$.

EXAMPLE 19

Using the procedure described in Example 1 but substituting BOC-Gly with the appropriate acids and protected amino acid the following compounds are obtained as the trifluroacetate salts:

(a) NAc-D2Nal-D4ClPhe$^2$-D3Pal$^3$-Ser$^4$-NMeTyr$^5$-DLys[N-epsilon-(N'-epsilon-Aminocaproyl)(N"-beta-Alanyl)-Nicotinyl]$^6$-Leu$^7$-Lys(N-epsilon-Isopropyl)$^8$-Pro$^9$-DAla$^{10}$NH$_2$. R$_t$=17.88 min; FAB Mass spec. m/e 1718 (M+H)$^+$. Amino Acid Analysis: 1.01 Ala; 1.00 Pro; 0.98 Lys(Isp); 1.00 Leu; 0.99 Lys; 0.91 NMeTyr; 0.37 Ser; 1.15 3Pal; 1.03 4ClPhe.

(b) NAc-D2Nal$^1$-D4ClPhe$^2$-D3Pal$^3$-Ser$^4$-NMeTyr$^5$-DLys[N-epsilon-Gly-Salicyl)$^6$-Leu$^7$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys[N-epsilon-Gly-Gly-Nicotinyl]$^6$-Leu$^7$-Lys(N-epsilon-Isopropyl)$^8$-Pro$^9$-DAla$^{10}$NH$_2$. R$_t$=16.74 min; FAB Mass spec. m/e 1648 (M+H)$^+$. Amino Acid Analysis: 1.02 Ala; 1.06 Pro; 0.94 Lys(Isp); 1.02 Leu; 0.98 Lys; 0.86 NMeTyr; 0.40 Ser; 1.06 3Pal; 1.04 4ClPhe.

(d) NAc-D2Nal$^1$-D4ClPhe$^2$-D3Pal$^3$-Ser$^4$-NMeTyr$^5$-DLys[N-epsilon-(N'-epsilon-Aminocaproyl)-Gly-Nicotinyl]$^6$-Leu$^7$-Lys(N-epsilon-Isopropyl)$^8$-Pro$^9$-DAla$^{10}$NH$_2$. R$_t$=17.16 min; FAB Mass spec. m/e 1704 (M+H)$^+$. Amino Acid Analysis: 1.00 Ala; 1.03 Pro; 0.94 Lys(Isp); 0.97 Leu; 0.99 Lys; 0.0.72 NMeTyr; 0.41 Ser; 0.86 3Pal; 1.03 4ClPhe.

(e) NAc-D2Nal$^1$-D4ClPhe$^2$-D3Pal$^3$-Ser$^4$-NMeTyr$^5$-DLys(N-epsilon-D3Pal-Nicotinyl)$^6$-Leu$^7$-Lys(N-epsilon-Isopropyl)$^8$-Pro$^9$-DAla$^{10}$NH$_2$.
(f) NAc-D2Nal$^1$-D4ClPhe$^2$-D3Pal$^3$-Ser$^4$-NMeTyr$^5$-DLys(DHis-alpha-Nicotinyl)$^6$-Leu$^7$-Lys(N-epsilon-Isopropyl)$^8$-Pro$^9$-DAla$^{10}$NH$_2$.
(g) NAc-D2Nal$^1$-D4ClPhe$^2$-D3Pal$^3$-Ser$^4$-NMeTyr$^5$-DLys(N-epsilon-DTyr)$^6$-Leu$^7$-Lys(N-epsilon-isopropyl)$^8$-Pro$^9$-DAla$^{10}$NH$_2$.
(h) NAc-D2Nal$^1$-D4ClPhe$^2$-D3Pal$^3$-Ser$^4$-NMeTyr$^5$-DLys[N-epsilon-DTyr(OMe)-Nicotinyl]$^6$-Leu$^7$-Lys(N-epsilon-Isopropyl)$^8$-Pro$^9$-DAla$^{10}$NH$_2$.

EXAMPLE 20

Using the procedure described in Example 2 but substituting furoic hydraazide with the appropriate acid hydrazide the following compounds are obtained as trifluorocetate salts:

(a) NAc-D2Nal$^1$-D4ClPhe$^2$-D3Pal$^3$-Ser$^4$-NMeTyr$^5$-DLys(N-epsilon-Azagly-Picolinyl)$^6$-Leu$^7$-Lys(N-epsilon-isopropyl)$^8$-Pro$^9$-DAla$^{10}$NH$_2$
(b) NAc-D2Nal$^1$-D4ClPhe$^2$-D3Pal$^3$-Ser$^4$-NMeTyr$^5$-DLys(N-epsilon-Azagly-3-Indoleacetyl)$^6$-Leu$^7$-Lys(N-epsilon-Isopropyl)$^8$-Pro$^9$-DAla$^1$-NH$_2$
(c) NAc-D2Nal$^1$-D4ClPhe$^2$-D3Pal$^3$-Ser$^4$-NMeTyr$^5$-DLys(N-epsilon-Azagly-Shikimyl)$^6$-Leu$^7$-Lys(N-epsilon-Isopropyl)$^8$-Pro$^9$-DAla$^{10}$NH$_2$
(d) NAc-D2Nal$^1$-D4ClPhe$^2$-D3Pal$^3$-Ser$^4$-NMeTyr$^5$-DLys(N-epsilon-Azagly-Quinoline-3-carbonyl)$^6$-Leu$^7$-Lys(N-epsilon-Isopropyl)$^8$-Pro$^9$-DAla$^{10}$NH$_2$
(e) NAc-D2Nal$^1$-D4ClPhe$^2$-D3Pal$^3$-Ser$^4$-NMeTyr$^5$-DLys(N-epsilon-Azagly-Pyrrole-2-carbonyl)$^6$-Leu$^7$-Lys(N-epsilon-Isopropyl)$^8$-Pro$^9$-DAla$^{10}$NH$_2$
(f) NAc-D2Nal$^1$-D4ClPhe$^2$-D3Pal$^3$-Ser$^4$-NMeTyr$^5$-DLys(N-epsilon-Azagly-Benzoyl)$^6$-Leu$^7$-Lys(N-epsilon-Isopropyl)$^8$-Pro$^9$-DAla$^{10}$NH$_2$
(g) NAc-D2Nal$^1$-D4ClPhe$^2$-D3Pal$^3$-Ser$^4$-NMeTyr$^5$-DLys(N-epsilon-Azagly-p-MeO-Benzoyl)$^6$-Leu$^7$-Lys(N-epsilon-isopropyl)$^8$-Pro$^9$-DAla$^{10}$NH$_2$
(h) NAc-D2Nal$^1$-D4ClPhe$^2$-D3Pal$^3$-Ser$^4$-NMeTyr$^5$-DLys(N-epsilon-Azagly-6-OH-Nicotinyl)$^6$-Leu$^7$-Lys(N-epsilon-isopropyl)$^8$-Pro$^9$-DAla$^{10}$NH$_2$
(i) NAc-D2Nal$^1$-D4ClPhe$^2$-D3Pal$^3$-Ser$^4$-NMeTyr$^5$-DLys(N-epsilon-Azagly-2-OH-Nicotinyl)$^6$-Leu$^7$-Lys(N-epsilon-isopropyl)$^8$-Pro$^9$-DAla$^{10}$NH$_2$
(j) NAc-D2Nal$^1$-D4ClPhe$^2$-D3Pal$^3$-Ser$^4$-NMeTyr$^5$-DLys(N-epsilon-Azagly-3-Furoyl)$^6$-Leu$^7$-Lys(N-epsilon-isopropyl)$^8$-Pro$^9$-DAla$^1$-NH$_2$
(k) NAc-D2Nal$^1$-D4ClPhe$^2$-D3Pal$^3$-Ser$^4$-NMeTyr$^5$-DLys(N-epsilon-Azagly-2-Naphthoyl)$^6$-Leu$^7$-Lys(N-epsilon-isopropyl)$^8$-Pro$^9$-DAla$^{10}$NH$_2$
(l) NAc-D2Nal$^1$-D4ClPhe$^2$-D3Pal$^3$-Ser$^4$-NMeTyr$^5$-DLys(N-epsilon-Azagly-Dihydroshikimyl)$^6$-Leu$^7$ -Lys(N-epsilon-isopropyl)$^8$-Pro$^9$-DAla$^{10}$NH$_2$
(m) NAc-D2Nal$^1$-D4ClPhe$^2$-D3Pal$^3$-Ser$^4$-NMeTyr$^5$-DLys(N-epsilon-Azagly-Acetyl)$^6$-Leu$^7$-Lys(N-epsilon-Isopropyl)$^8$-Pro$^9$-DAla$^{10}$NH$_2$
(n) NAc-D2Nal$^1$-D4ClPhe$^2$-D3Pal$^3$-Ser$^4$-NMeTyr$^5$-DLys(N-epsilon-Azagly-Formyl)$^6$-Leu$^7$-Lys(N-epsilon-Isopropyl)$^8$-Pro$^9$-DAla$^{10}$NH$_2$
(o) NAc-D2Nal$^1$-D4ClPhe$^2$-D3Pal$^3$-Ser$^4$-NMeTyr$^5$-DLys(N-epsilon-Azagly-Propionyl)$^6$-Leu$^7$-Lys(N-epsilon-Isopropyl)$^8$-Pro$^9$-DAla$^{10}$NH$_2$
(p) NAc-D2Nal$^1$-D4ClPhe$^2$-D3Pal$^3$-Ser$^4$-NMeTyr$^5$-DLys(N-epsilon-Azagly-Cyclohexyl)$^6$-Leu$^7$-Lys(N-epsilon-Isopropyl)$^8$-Pro$^9$-DAla$^{10}$NH$_2$
(q) NAc-D2Nal$^1$-D4ClPhe$^2$-D3Pal$^3$-Ser$^4$-NMeTyr$^5$-DLys(N-epsilon-Azagly-1-Adamantylacetyl)$^6$-Leu$^7$-Lys(N-epsilon-Isopropyl)$^8$-Pro$^9$-DAla$^{10}$NH$_2$
(r) NAc-D2Nal$^1$-D4ClPhe$^2$-D3Pal$^3$-Ser$^4$-NMeTyr$^5$-DLys(N-epsilon-Azagly-6-Me-Nicotinyl)$^6$-Leu$^7$-Lys(N-epsilon-Isopropyl)$^8$-Pro$^9$-DAla$^{10}$NH$_2$
(s) NAc-D2Nal$^1$-D4ClPhe$^2$-D3Pal$^3$-Ser$^4$-NMeTyr$^5$-DLys(N-epsilon-Azagly-2-Me-Nicotinyl)$^6$-Leu$^7$ -Lys(N-epsilon-isopropyl)$^8$-Pro$^9$-DAla$^{10}$NH$_2$
(t) NAc-D2Nal$^1$-D4ClPhe$^2$-D3Pal$^3$-Ser$^4$-NMeTyr$^5$-DLys(N-epsilon-Azagly-Pyrazine-2-carbonyl)$^6$-Leu$^7$-Lys(N-epsilon-Isopropyl)$^8$-Pro$^9$-DAla$^{10}$NH$_2$
(u) NAc-D2Nal$^1$-D4ClPhe$^2$-D3Pal$^3$-Ser$^4$-NMeTyr$^5$-DLys[(N-epsilon-Azagly-(2-pyrimidylthioacetyl)]$^6$-Leu$^7$-Lys(N-epsilon-Isopropyl)$^8$-Pro$^9$-DAla$^{10}$NH$_2$
(v) NAc-D2Nal$^1$-D4ClPhe$^2$-D3Pal$^3$-Ser$^4$-NMeTyr$^5$-DLys[N-epsilon-Azagly-(3-Pyridylacetyl)]$^6$-Leu$^7$-Lys(N-epsilon-isopropyl)$^8$-Pro$^9$-DAla$^{10}$NH$_2$
(w) NAc-D2Nal$^1$-D4ClPhe$^2$-D3Pal$^3$-Ser$^4$-NMeTyr$^5$-DLys]N-epsilon-Azagly-(2,5-di-MeO)Nicotinyl]$^6$-Leu$^7$-Lys(N-epsilon-Isopropyl)$^8$-Pro$^9$-DAla$^{10}$NH$_2$
(x) NAc-D2Nal$^1$-D4ClPhe$^2$-D3Pal$^3$-Ser$^4$-NMeTyr$^5$-DLys(N-epsilon-Azagly-2-pyrrolecarbonyl)$^6$-Leu$^7$-Lys(N-epsilon-Isopropyl)$^8$-Pro$^9$-DAla$^9$NH$_2$
(y) NAc-D2Nal$^1$-D4ClPhe$^2$-D3Pal$^3$-Ser$^4$-NMeTyr$^5$-DLys(N-epsilon-Azagly-2-Indolecarbonyl)$^6$-Leu$^7$-Lys(N-epsilon-Isopropyl)$^8$-Pro$^9$-DAla$^{10}$NH$_2$
(z) NAc-D2Nal$^1$-D4ClPhe$^2$-D3Pal$^3$-Ser$^4$-NMeTyr$^5$-DLys(N-epsilon-Azagly-6-chloronicotinyl)$^6$-Leu$^7$-Lys(N-epsilon-Isopropyl)$^8$-Pro$^9$-DAla$^{10}$NH$_2$
(aa) NAc-D2Nal$^1$-D4ClPhe$^2$-D3Pal$^3$-Ser$^4$-NMeTyr$^5$-DLys(N-epsilon-Azagly-5-Me-Salicyl)$^6$-Leu$^7$-Lys(N-epsilon-Isopropyl)$^8$-Pro$^9$-DAla$^{10}$NH$_2$
(ab) NAc-D2Nal$^1$-D4ClPhe$^2$-D3Pal$^3$-Ser$^4$-NMeTyr$^5$-DLys(N-epsilon-Azagly-5-MeO-Indole-2-carbonyl)$^6$-Leu$^7$-Lys(N-epsilon-Isopropyl)$^8$-Pro$^9$-DAla$^{10}$NH$_2$
(ac) NAc-D2Nal$^1$-D4ClPhe$^2$-D3Pal$^3$-Ser$^4$-NMeTyr$^5$-DLys(N-epsilon-Azagly-Benzofuran-2-carbonyl)$^6$-Leu$^7$-Lys(N-epsilon-Isopropyl)$^8$-Pro$^9$-DAla$^{10}$NH$_2$
(ad) NAc-D2Nal$^1$-D4ClPhe$^2$-D3Pal$^3$-Ser$^4$-NMeTyr$^5$-DLys(N-epsilon-Azagly-7-MeO-Benzofuran-2-carbonyl)$^6$-Leu$^7$-Lys(N-epsilon-Isopropyl)$^8$-Pro$^9$-DAla$^{10}$NH$_2$

EXAMPLE 21

NAc-D2Nal$^1$-D4ClPhe$^2$-D3Pal$^3$-Ser$^4$-NMeTyr$^5$-DLys(N-epsilon-Azagly-Azagly-2-Furoyl)$^6$-Leu$^7$-Lys(N-epsilon-Isopropyl)$^8$-Pro$^9$-DAla$^{10}$NH$_2$ The procedure described in Example 1 is used to remove of the FMOC group. Instead of coupling with BOC-Gly the peptide is treated with a solution of carbonyldiimidazole (0.9 g) in DMF (18 ml) for 15 minutes, washed (×3) with methylene chloride, and then reacted overnight with a solution of anhydrous hydrazine (5 ml) in DMF (20 ml). The resin is washed again (×3) with methylene chloride and reacted with a solution of carbonyldiimidazole (0.9 g) in DMF (18 ml) for 15 minutes, washed (×3) with methylene chloride, and then reacted with a solution of 2-furoic hydrazide (0.53 g) in DMF (18 ml) overnight. The resin is washed (×3) with methylene chloride, dried overnight over P$_2$O$_5$, and treated with dry HF/anisole at 0° C. for 1 h. After work-up, lyophilization, and HPLC purification NAc-D2Nal-D4ClPhe-D3Pal-Ser-NMeTyr-DLys(N-epsilon-Azagly-Azagly-2-Furoyl)-Leu-Lys(N-epsilon-Isopropyl)-Pro-DAlaNH$_2$ is obtained as the trifluoroacetate salt.

EXAMPLE 22

The procedure described in Example 21 is used but substituting the appropriate acid hydrazides instead of 2-furoic acid hydrazide, after work-up, HPLC purification, and lyophilization the following compounds are obtained as the trifluoroacetate salts:

(a) NAc-D2Nal$^1$-D4ClPhe-D3Pal$^3$-Ser$^4$-NMeTyr$^5$-DLys(N-epsilon-Azagly-Azagly-3-Furoyl)-Leu-Lys(N-epsilon-Isopropyl)-Pro-DAlaNH$_2$ (b) NAc-D2Nal$^1$-D4ClPhe$^2$-D3Pal$^3$-Ser$^4$-NMeTyr$^5$-DLys (N-epsilon-Azagly-Azagly-Nicotinyl)$^6$-Leu$^7$-Lys(N-epsilon-Isopropyl)$^8$-Pro$^9$-DAla$^{10}$NH$_2$ (c) NAc-D2Nal$^1$-D4ClPhe$^2$-D3Pal$^3$-Ser$^4$-NMeTyr$^5$-DLys (N-epsilon-Azagly-Azagly-Shikimyl)$^6$-Leu$^7$-Lys(N-epsilon-Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys (N-epsilon-Azagly-Azagly-Salicyl)$^6$-Leu$^7$-Lys(N-epsilon-Isopropyl)$^8$-Pro$^9$-DAla$^{10}$NH$_2$ (e) NAc-D2Nal$^1$-D4ClPhe$^2$-D3Pal$^3$-Ser$^4$-NMeTyr$^5$-DLys (N-epsilon-Azagly-Azagly-Quinoline-3-carbonyl)$^6$-Leu$^7$-Lys(N-epsilon-Isopropyl)$^8$-Pro$^9$-DAla$^{10}$NH$_2$ (f) NAc-D2Nal$^1$-D4ClPhe$^2$-D3Pal$^3$-Ser$^4$-NMeTyr$^5$-DLys (N-epsilon-Azagly-Azagly-Benzofuran-2-carbonyl)$^6$-Leu$^7$-Lys(N-epsilon-Isopropyl)$^8$-Pro$^9$-DAla$^{10}$NH$_2$ (g) NAc-D2Nal$^1$-D4ClPhe$^2$-D3Pal$^3$-Ser$^4$-NMeTyr$^5$-DLys (N-epsilon-Azagly-Azagly-Indole-2-carbonyl)$^6$-Leu$^7$-Lys(N-epsilon-Isopropyl)$^8$-Pro$^9$-DAla$^{10}$NH$_2$ (h) NAc-D2Nal$^1$-D4ClPhe$^2$-D3Pal$^3$-Ser$^4$-NMeTyr$^5$-DLys (N-epsilon-Azagly-Azagly-Pyrazine-2-carbonyl)$^6$-Leu$^7$-Lys(N-epsilon-Isopropyl)$^8$-Pro$^9$-DAla$^{10}$NH$_2$ (i) NAc-D2Nal$^1$-D4ClPhe$^2$-D3Pal$^3$-Ser$^4$-NMeTyr$^5$-DLys (N-epsilon-Azagly-Azagly-Acetyl)$^6$-Leu$^7$-Lys(N-epsilon-Isopropyl)$^8$-Pro$^9$-DAla$^{10}$NH$_2$ (j) NAc-D2Nal$^1$-D4ClPhe$^2$-D3Pal$^3$-Ser$^4$-NMeTyr$^5$-DLys (N-epsilon-Azagly-Azagly-propionyl)$^6$-Leu$^7$-Lys(N-epsilon-isopropyl)$^8$-Pro$^9$-DAla$^{10}$NH$_2$ (k) NAc-D2Nal$^1$-D4ClPhe$^2$-D3Pal$^3$-Ser$^4$-NMeTyr$^5$-DLys (N-epsilon-Azagly-Azagly-Formyl)$^6$-Leu$^7$-Lys(N-epsilon-Isopropyl)$^8$-Pro$^9$-DAla$^{10}$NH$_2$ (l) NAc-D2Nal$^1$-D4ClPhe$^2$-D3Pal$^3$-Ser$^4$-NMeTyr$^5$-DLys (N-epsilon-Azagly-Azagly-Dihydroshikimyl)$^6$-Leu$^7$-Lys (N-epsilon-Isopropyl)$^8$-Pro$^9$DAla$^{10}$NH$_2$ (m) NAc-D2Nal$^1$-D4ClPhe$^2$-D3Pal$^3$-Ser$^4$-NMeTyr$^5$-DLys (N-epsilon-Azagly-Azagly-Benzoyl)$^6$-Leu$^7$-Lys(N-epsilon-isopropyl)$^8$-Pro$^9$-DAla$^{10}$NH$_2$ (n) NAc-D2Nal$^1$-D4ClPhe$^2$-D3Pal$^3$-Ser$^4$-NMeTyr$^5$-DLys (N-epsilon-Azagly-Azagly-Tetrahydro-2-furoyl)$^6$-Leu$^7$-Lys(N-epsilon-Isopropyl)$^8$-Pro$^9$-DAla$^{10}$NH$_{2.(o)}$ NAc-D2Nal$^1$-D4ClPhe$^2$-D3Pal$^3$-Ser$^4$-NMeTyr$^5$-DLys(N-epsilon-Azagly-Azagly-Benzofurane-3-carbonyl)$^6$-Leu$^7$-Lys(N-epsilon-isopropyl)$^8$-Pro$^9$-DAla$^{10}$NH$_2$

EXAMPLE 23

NAc-D2Nal$^1$-D4ClPhe$^2$-D3Pal$^3$-Ser$^4$-NMeTyr$^5$-DLys(N-epsilon-Gly-Azagly-Nicotinyl)$^6$-Leu$^7$-Lys(N-epsilon-isopropyl)$^8$-Pro$^9$-DAla$^{10}$NH$_2$ The procedure described in Example 1 is used up through the coupling with BOC-Gly followed by deblocking and wash with base. The resin is then treated with carbonyldiimidazole (0.9 g) in DMF (20 ml) for 15 minutes, washed (×3) with methylene chloride and reacted overnight with nicotinic hydrazide (0.575 g) in DMF (20 ml), washed (×3) with methylene chloride and dried overnight. The peptide is then cleaved from the resin using HF/anisole at 0° C. for 1 h as described above. After work-up, purification and lyophilization NAc-D2Nal$^1$-D4ClPhe$^2$-D3Pal$^3$-Ser$^4$-NMeTyr$^5$-DLys(N-epsilon-Gly-Azagly-Nicotinyl)$^6$-Leu$^7$-Lys(N-epsilon-Isopropyl)$^8$-Pro$^9$-DAla$^{10}$NH$_2$ is obtained as the trifluoroacetate salt; R$_f$=15.96 min; FAB Mass spec. m/e 1649 (M+H)$^+$. Amino Acid Analysis: 1.00 Ala; 1.01 Pro; 0.99 Lys(Isp); 1.01 Leu; 0.99 Lys; 0.74 NMeTyr; 0.42 Ser; 1.05 3Pal; 1.07 4ClPhe.

EXAMPLE 24

The procedure described in Example 23 is used but substituting the appropriate acid hydrazides instead of nicotinic hydrazide the following compounds are obtained as the trifluoroacetate salts:

(a) NAc-D2Nal$^1$-D4ClPhe$^2$-D3Pal$^3$-Ser$^4$-NMeTyr$^5$-DLys (N-epsilon-Gly-Azagly-2-Furoyl)$^6$-Leu$^7$-Lys(N-epsilon-Isopropyl)$^8$-Pro$^9$-DAla$^{10}$NH$_2$.

(b) NAc-D2Nal$^1$-D4ClPhe$_2$-D3Pal$^3$-Ser$^4$-NMeTyr$^5$-DLys (N-epsilon-Gly-Azagly-Benzofurane-2-carbonyl)$^6$-Leu$^8$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys (N-epsilon-Gly-Azagly-Shikimyl)$^6$-Leu$^7$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys (N-epsilon-Gly-Azagly-Benzoyl)$^6$-Leu$^7$-Lys(N-epsilon-Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys (N-epsilon-Gly-Azagly-Acetyl)$^6$-Leu$^7$-Lys(N-epsilon-Isopropyl)$^8$-Pro$^9$-DAla$^{10}$NH$_2$ (e) NAc-D2Nal$^1$-D4ClPhe$^2$-D3Pal$^3$-Ser$^4$-NMeTyr$^5$-DLys (N-epsilon-Gly-Azagly-2-Furoyl)$^6$-Leu$^7$-Lys(N-epsilon-isopropyl)$^8$-Pro$^9$-DAla$^{10}$NH$_2$ (f) NAc-D2Nal$^1$-D4ClPhe$^2$-D3Pal$^3$-Ser$^4$-NMeTyr$^5$-DLys (N-epsilon-Gly-Azagly-Formyl)$^6$-Leu$^7$-Lys(N-epsilon-Isopropyl)$^8$-Pro$^9$-DAla$^{10}$NH$_2$ (g) NAc-D2Nal$^1$-D4ClPhe$^2$-D3Pal$^3$-Ser$^4$-NMeTyr$^5$-DLys (N-epsilon-Gly-Azagly-Picolinyl)$^6$-Leu$^7$-Lys(N-epsilon-isopropyl)$^8$-Pro$^9$-DAla$^{10}$NH$_2$ (h) NAc-D2Nal$^1$-D4ClPhe$^2$-D3Pal$^3$-Ser$^4$-NMeTyr$^5$-DLys (N-epsilon-Gly-Azagly-Salicyl)$^6$-Leu$^7$-Lys(N-epsilon-Isopropyl)$^8$-Pro$^9$-DAla$^{10}$NH$_2$ (i) NAc-D2Nal$^1$-D4ClPhe$^2$-D3Pal$^3$-Ser$^4$-NMeTyr$^5$-DLys (N-epsilon-Gly-Azagly-Pyrazinoyl)$^6$-Leu$^7$-Lys(N-epsilon-Isopropyl)$^8$-Pro$^9$-DAla$^{10}$NH$_2$ (j) NAc-D2Nal$^1$-D4ClPhe$^2$-D3Pal$^3$-Ser$^4$-NMeTyr$^5$-DLys (N-epsilon-Gly-3-quinolinecarbonylyl)$^6$-Leu$^7$-Lys(N-epsilon-Isopropyl)$^8$-Pro$^9$-DAla$^{10}$NH$_2$

EXAMPLE 25

The procedure described in Example 23 is used but substituting the appropriate BOC-amino acid instead of BOC-Gly the following compounds are obtained as the trifluoroacetate salts:

(a) NAc-D2Nal$^1$-D4ClPhe$^2$-D3Pal$^3$-Ser$^4$-NMeTyr$^5$-DLys [N-epsilon-(beta-Alanyl)-Azagly-Nicotinyl]$^6$-Leu$^7$-Lys (N-epsilon-Isopropyl)$^8$-Pro$^9$-DAla$^{10}$NH$_2$.

(b) NAc-D2Nal$^1$-D4ClPhe$^2$-D3Pal$^3$-Ser$^4$-NMeTyr$^5$-DLys [N-epsilon-(gamma-Aminobutyryl)-Azagly-Nicotinyl]$^6$-Leu$^7$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys [N-epsilon-(5-Aminovaleryl)-Azagly-Nicotinyl]$^6$-Leu$^7$-Lys(N-epsilon-Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys[N-epsilon-(epsilon-Aminocaproyl)-Azagly-Nicotinyl]$^6$-Leu$^7$-Lys(N-epsilon-Isopropyl)$^8$-Pro$^9$-DAla$^{10}$NH$_2$; R$_f$=17.61 min; FAB Mass spec. m/e 1705 (M+H)$^+$. Amino Acid Analysis: 1.01 Ala; 1.01 Pro; 0.92 Lys(Isp); 0.99 Leu; 0.97 Lys; 1.03 NMeTyr; 0.33 Ser; 1.00 3Pal; 1.02 4ClPhe.

(e) NAc-D2Nal$^1$-D4ClPhe$^2$-D3Pal$^3$-Ser$^4$-NMeTyr$^5$-DLys [N-epsilon-(7-Aminoheptanoyl)-Azagly-Nicotinyl]$^6$-Leu$^7$-Lys(N-epsilon-Isopropyl)$^8$-Pro$^9$-DAla$^{10}$NH$_2$.

(f) NAc-D2Nal$^1$-D4ClPhe$^2$-D3Pal$^3$-Ser$^4$-NMeTyr$^5$-DLys [N-epsilon-(11-Aminoundecanoyl)-Azagly-Nicotinyl]$^6$-Leu$^7$-Lys(N-epsilon-Isopropyl)$^8$-Pro$^9$ -DAla$^{10}$NH$_2$;

$R_t$=26.59 min; FAB Mass spec. m/e 1776 (M+H)⁺. Amino Acid Analysis: 1.01 Ala; 1.01 Pro; 0.97 Lys(Isp); 1.00 Leu; 0.99 Lys; 0.87 NMeTyr; 0.58 Ser; 0.94 3Pal; 0.94 4ClPhe.

EXAMPLE 26

The procedure described in Example 25 is used but substituting 2-Furoic hydrazide instead of Nicotinic hydrazide the following compounds are obtained as the trifluoroacetate salts:

(a) NAc-D2Nal$^1$-D4ClPhe$^2$-D3Pal$^3$-Ser$^4$-NMeTyr$^5$-DLys [N-epsilon-(beta-Alanyl)-Azagly-2-Furoyl]$^6$-Leu$^7$-Lys (N-epsilon-Isopropyl)$^8$-Pro$^9$-DAla$^{10}$NH$_2$.

(b) NAc-D2Nal$^1$-D4ClPhe$^2$-D3Pal$^3$-Ser$^4$-NMeTyr$^5$-DLys [N-epsilon-(gamma-Aminobutyryl)-Azagly-2-Furoyl]$^6$-Leu$^7$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys [N-epsilon-(5-Aminovaleryl)-Azagly-2-Furoyl]$^6$-Leu$^7$-Lys(N-epsilon-Isopropyl)$^8$-Pro$^9$-DAla$^{10}$NH$_2$.

(d) NAc-D2Nal$^1$-D4ClPhe$^2$-D3Pal$^3$-Ser$^4$-NMeTyr$^5$-DLys [N-epsilon-(epsilon-Aminocaproyl)-Azagly-2-Furoyl]$^6$-Leu$^7$-Lys(N-epsilon-Isopropyl)$^8$-Pro$^9$-DAla$^{10}$NH$_2$; $R_t$=26.10 min; FAB Mass spec. m/e 1694 (M+H)⁺. Amino Acid Analysis: 1.04 Ala; 0.99 Pro; 0.94 Lys(Isp); 0.99 Leu; 0.97 Lys; 1.18 NMeTyr; 0.44 Ser; 0.99 3Pal; 0.99 4ClPhe.

(e) NAc-D2Nal$^1$-D4ClPhe$^2$-D3Pal$^3$-Ser$^4$-NMeTyr$^5$-DLys [N-epsilon-(7-Aminoheptanoyl)-Azagly-2-Furoyl]$^6$-Leu$^7$-Lys(N-epsilon-Isopropyl)$^8$-Pro$^9$-DAla$^{10}$NH$_2$.

(f) NAc-D2Nal$^1$-D4ClPhe$^2$-D3Pal$^3$-Ser$^4$-NMeTyr$^5$-DLys [N-epsilon-(11-Aminoundecanoyl)-Azagly-2-Furoyl]$^6$-Leu$^7$-Lys(N-epsilon-Isopropyl)$^8$-Pro$^9$-DAla$^{10}$NH$_2$.

EXAMPLE 27

NAc-D2Nal$^1$-D4ClPhe$^2$-D3Pal$^3$-Ser$^4$-NMeTyr$^5$-DLys(N-epsilon-Azagly-D-Tyrosyl-Acetyl)$^6$-Leu$^7$-Lys(N-epsilon-Isopropyl)$^8$-Pro$^9$-DAla$^{10}$NH$_2$ The procedure described in Example 2 is used but substituting N-alpha-Acetyl-D-Tyrosyl hydrazide instead of 2-furoic hydrazide, after work-up, purification, and lyophilization NAc-D2Nal-D4ClPhe-D3Pal-Ser-NMeTyr-DLys(N-epsilon-Azagly-D-Tyrosyl-Acetyl)-Leu-Lys(N-epsilon-Isopropyl)-Pro-DAlaNH$_2$ is obtained.

EXAMPLE 28

The procedure described in Example 27 is used but substituting N-alpha-Acetyl-D-or L-Amino Acid hydrazides instead of N-alpha-Acetyl-D-Tyrosyl hydrazide, after work-up, purification, and lyophilization the following compounds are obtained:

(a) NAc-D2Nal$^1$-D4ClPhe-D3Pal$^3$-Ser$^4$-NMeTyr-DLys(N-epsilon-Azagly-DPhenylalanyl-Acetyl)$^6$-Leu$^7$-Lys(N-epsilon-isopropyl)$^8$-Pro$^9$-DAla$^{10}$NH$_2$ (b) NAc-D2Nal$^1$-D4ClPhe$^2$-D3Pal$^3$-Ser$^4$-NMeTyr$^5$-DLys (N-epsilon-Azagly-DHistidyl-Acetyl)$^6$-Leu$^7$-Lys(N-epsilon-Isopropyl)$^8$ -Pro$^9$-DAla$^{10}$NH$_2$ (c) NAc-D2Nal$^1$-D4ClPhe$^2$-D3Pal$^3$-Ser$^4$-NMeTyr$^5$-DLys (N-epsilon-Azagly-D-3-Pyridylalanyl-Acetyl)$^6$-Leu$^7$-Lys (N-epsilon-Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys (N-epsilon-Azagly-Tyrosyl-Acetyl)$^6$-Leu$^7$-Lys(N-epsilon-Isopropyl)$^8$-Pro$^9$-DAla$^{10}$NH$_2$ (e) NAc-D2Nal$^1$-D4ClPhe$^2$-D3Pal$^3$-Ser$^4$-NMeTyr$^5$-DLys (N-epsilon-Azagly-DSeryl-N-Acetyl)$^6$-Leu$^7$-Lys(N-epsilon-Isopropyl)$^8$-Pro$^9$-DAla$^{10}$NH$_2$ (f) NAc-D2Nal$^1$-D4ClPhe$^2$-D3Pal$^3$-Ser$^4$-NMeTyr$^5$-DLys (N-epsilon-Azagly-DAlanyl-Acetyl)$^6$-Leu$^7$-Lys(N-epsilon-Isopropyl)$^8$-Pro$^9$-DAla$^{10}$NH$_2$ (g) NAc-D2Nal$^1$-D4ClPhe$^2$-D3Pal$^3$-Ser$^4$-NMeTyr$^5$-DLys (N-epsilon-Azagly-Phenylalanyl-Acetyl)$^6$-Leu$^7$-Lys(N-epsilon-Isopropyl)$^8$-Pro$^9$-DAla$^{10}$NH$_2$ (h) NAc-D2Nal$^1$-D4ClPhe$^2$-D3Pal$^3$-Ser$^4$-NMeTyr$^5$-DLys (N-epsilon-Azagly-DLeucyl-Acetyl)$^6$-Leu$^7$-Lys(N-epsilon-Isopropyl)$^8$-Pro$^9$-DAla$^{10}$NH$_2$ (i) NAc-D2Nal$^1$-D4ClPhe$^2$-D3Pal$^3$-Ser$^4$-NMeTyr$^5$-DLys (N-epsilon-Azagly-DCitrullyl-Acetyl)$^6$-Leu$^7$-Lys(N-epsilon-Isopropyl)$^8$-Pro$^9$-DAla$^{10}$NH$_2$ (j) NAc-D2Nal$^1$-D4ClPhe$^2$-D3Pal$^3$-Ser$^4$-NMeTyr$^5$-DLys (N-epsilon-Azagly-DTryptyl-Acetyl)$^6$-Leu$^7$-Lys(N-epsilon-Isopropyl)$^8$-Pro$^9$-DAla$^{10}$NH$_2$ (k) NAc-D2Nal$^1$-D4ClPhe$^2$-D3Pal$^3$-Ser$^4$-NMeTyr$^5$-DLys (N-epsilon-Azagly-DThreonyl-Acetyl)$^6$-Leu$^7$-Lys(N-epsilon-Isopropyl)$^8$-Pro$^9$-DAla$^{10}$NH$_2$

EXAMPLE 29

The procedure described in Example 23 is used but substituting nicotinic hydrazide with the appropriate N-alpha-Acetyl-D-or L-Amino Acid hydrazides, after work-up, purification, and lyophilization the following compounds are obtained:

(a) NAc-D2Nal$^1$-D4ClPhe$^2$-D3Pal$^3$-Ser$^4$-NMeTyr$^5$-DLys (N-epsilon-Gly-Azagly-DPhenylalanyl-Acetyl)$^6$-Leu$^7$-Lys(N-epsilon-Isopropyl)$^8$-Pro$^9$-DAla$^{10}$NH$_2$ (b) NAc-D2Nal$^1$-D4ClPhe$^2$-D3Pal$^3$-Ser$^4$-NMeTyr$^5$-DLys (N-epsilon-Gly-Azagly-DHystidyl-Acetyl)$^6$-Leu$^7$-Lys(N-epsilon-Isopropyl)$^8$-Pro$^9$-DAla$^{10}$NH$_2$ (c) NAc-D2Nal$^1$-D4ClPhe$^2$-D3Pal$^3$-Ser$^4$-NMeTyr$^5$-DLys (N-epsilon-Gly-Azagly-D-3-Pyridylalanyl-Acetyl)$^6$-Leu$^7$-Lys(N-epsilon-Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys (N-epsilon-Gly-Azagly-Tyrosyl-Acetyl)$^6$-Leu$^7$-Lys(N-epsilon-Isopropyl)$^8$-Pro$^9$-DAla$^{10}$NH$_2$ (e) NAc-D2Nal$^1$-D4ClPhe$^2$-D3Pal$^3$-Ser$^4$-NMeTyr$^5$-DLys (N-epsilon-Gly-Azagly-DSeryl-N-Acetyl)$^6$-Leu$^7$-Lys(N-epsilon-Isopropyl)$^8$-Pro$^9$-DAla$^{10}$NH$_2$ (f) NAc-D2Nal$^1$-D4ClPhe$^2$-D3Pal$^3$-Ser$^4$-NMeTyr$^5$-DLys (N-epsilon-Gly-Azagly-DAlanyl-Acetyl)$^6$-Leu$^7$-Lys(N-epsilon-Isopropyl)$^8$-Pro$^9$-DAla$^{10}$NH$_2$ (g) NAc-D2Nal$^1$-D4ClPhe$^2$-D3Pal$^3$-Ser$^4$-NMeTyr$^5$-DLys (N-epsilon-Gly-Azagly-Phenylalanyl-Acetyl)$^6$-Leu$^7$-Lys (N-epsilon-Isopropyl)$^8$-Pro$^9$-DAla$^{10}$NH$_2$ (h) NAc-D2Nal$^1$-D4ClPhe$^2$-D3Pal$^3$-Ser$^4$-NMeTyr$^5$-DLys (N-epsilon-Azagly-Gly-DLeucyl-N-alpha-Acetyl)$^6$-Leu$^7$-Lys(N-epsilon-Isopropyl)$^8$-Pro$^9$-DAla$^{10}$NH$_2$ (i) NAc-D2Nal$^1$-D4ClPhe$^2$-D3Pal$^3$-Ser$^4$-NMeTyr$^5$-DLys (N-epsilon-Gly-Azagly-DCitrullyl-Acetyl)$^6$-Leu$^7$-Lys(N-epsilon-Isopropyl)$^8$-Pro$^9$-DAla$^{10}$NH$_2$ (j) NAc-D2Nal$^1$-D4ClPhe$^2$-D3Pal$^3$-Ser$^4$-NMeTyr$^5$-DLys (N-epsilon-Gly-Azagly-DCitrullyl-Acetyl)$^6$-Leu$^7$-Lys(N-epsilon. Isopropyl)$^8$-Pro$^9$-DAla$^{10}$NH$_2$ (k) NAc-D2Nal$^1$-D4ClPhe$^2$-D3Pal$^3$-Ser$^4$-NMeTyr$^5$-DLys (N-epsilon-Gly-Azagly-DTryptyl-Acetyl)$^6$-Leu$^7$-Lys(N-epsilon-Isopropyl)$^8$-Pro$^9$-DAla$^{10}$NH$_2$

EXAMPLE 30

NAc-D2Nal$^1$-D4ClPhe$^2$-D3Pal$^3$-Ser$^4$-NMeTyr$^5$-DLys[N-epsilon-(N'-Carbonyl-Diaminoethane-N"-Nicotinyl)]$^6$-Leu$^7$-Lys(N-epsilon-Isopropyl)$^8$-Pro$^9$-DAla$^{10}$NH$_2$ The procedure described in Example 14 is used but substituting BOC-Lys(N-epsilon-Cbz, Isopropyl) for BOC-Arg(Tos), after work-up, purification, and lyophilization NAc-D2Nal$^1$-D4ClPhe$^2$-D3Pal$^3$-Ser$^4$-NMeTyr$^5$-DLys[N-epsilon-(N'-Carbonyl-Diaminoethane-N"-Nicotinyl)]$^6$-Leu$^7$-Lys(N-epsilon-Isopropyl)$^8$-Pro$^9$-DAla$^{10}$NH$_2$ is obtained as the trifluoroacetate salt.

EXAMPLE 31

The procedure described in Example 30 is used but substituting the appropriate acids for nicotinic acid, after work-up, purification, and lyophilization the following compounds are obtained:

(a) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Pyrazinoyl)]$^6$-Leu$^7$-Lys(N-epsilon-Isopropyl)$^8$-Pro$^9$-DAla$^{10}$NH$_2$.

(b) NAc-D2Nal$^1$-D4ClPhe$^2$-D3Pal$^3$-Ser$^4$-NMeTyr$^5$-DLys[N-epsilon-(N'-Carbonyl-Diaminoethane-N''-2-Furoyl)]$^6$-Leu$^7$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Benzofuran-2-carbonyl)]$^6$-Leu$^7$-Lys(N-epsilon-isopropyl)$^8$-Pro$^9$-DAla$^{10}$NH$_2$.

(d) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Shikimyl)]$^6$-Leu$^7$-Lys(N-epsilon-Isopropyl)$^8$-Pro$^9$-DAla$^{10}$NH$_2$.

(e) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Benzoyl)]$^6$-Leu$^7$-Lys(N-epsilon-Isopropyl)$^8$-Pro$^9$-DAla$^{10}$NH$_2$.

(f) NAc-D2Nal$^1$-D4CLPhe$^2$-D3Pal$^3$-Ser$^4$-NMeTyr$^5$-DLys[N-epsilon-(N'-Carbonyl-Diaminoethane-N''-Acetyl)]$^6$-Leu$^7$-Lys(N-epsilon-Isopropyl)$^8$-Pro$^9$-DAla$^{10}$NH$_2$.

(g) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Formyl)]$^6$-Leu$^7$-Lys(N-epsilon-Isopropyl)$^8$-Pro$^9$-DAla$^{10}$NH$_2$.

(h) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Salicyl)]$^6$-Leu$^7$-Lys(N-epsilon-Isopropyl)$^8$-Pro$^9$-DAla$^{10}$NH$_2$.

(i) NAc-D2Nal$^1$-D4ClPhe$^2$-D3Pal$^3$-Ser$^4$-NMeTyr$^5$-DLys[N-epsilon-(N'-Carbonyl-Diaminoethane-N''-Picolinyl)]$^6$-Leu$^7$-Lys(N-epsilon-Isopropyl)$^8$-Pro$^9$-DAla$^{10}$NH$_2$.

(j) NAc-D2Nal$^1$-D4ClPhe$^2$-D3Pal$^3$-Ser$^4$-NMeTyr$^5$-DLys[N-epsilon-(N'-Carbonyl-Diaminoethane-N''-3-quinolinecarbonylyl)]$^6$-Leu$^7$-Lys(N-epsilon-Isopropyl)$^8$-Pro$^9$-DAla$^{10}$NH$_2$.

EXAMPLE 32

The procedure described in Example 30 is used but substituting the appropriate diaminoalkane for 1,2-diaminoethane, after work-up, purification, and lyophilization the following compounds are obtained:

(a) NAc-D2Nal$^1$-D4ClPhe$^2$-D3Pal$^3$-Ser$^4$NMeTyr-DLys[N-epsilon-(N'-Carbonyl-Diaminopropane-N''-Nicotinyl)]-Leu-Lys(N-epsilon-Isopropyl)$^8$-Pro$^9$-DAla$^{10}$NH$_2$.

(b) NAc-D2Nal$^1$-D4ClPhe$^2$-D3Pal$^3$-Ser$^4$-NMeTyr$^5$-DLys[N-epsilon-(N'-Carbonyl-Diaminobutane-N''-Nicotinyl)]$^6$-Leu$^7$-Lys(N-epsilon-Isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys[N-epsilon-(N'-Carbonyl-Diaminopentan-N''-Nicotinyl)]$^6$-Leu$^7$-Lys(N-epsilon-Isopropyl)$^8$-Pro$^9$-DAla$^{10}$NH$_2$.

(d) NAc-D2Nal$^1$-D4ClPhe$^2$-D3Pal$^3$-Ser$^4$-NMeTyr$^5$-DLys[N-epsilon-(N'-Carbonyl-Diaminohexane-N''-Nicotinyl)]$^6$-Leu$^7$-Lys(N-epsilon-Isopropyl)$^8$-Pro$^9$-DAla$^{10}$NH$_2$.

(e) NAc-D2Nal$^1$-D4ClPhe$^2$-D3Pal$^3$-Ser$^4$-NMeTyr$^5$-DLys[N-epsilon-(N'-Carbonyl-Diaminooctane-N''-Nicotinyl)]$^6$-Leu$^7$-Lys(N-epsilon-Isopropyl)$^8$-Pro$^9$-DAla$^{10}$NH$_2$.

EXAMPLE 33

NAc-D2Nal$^1$-D4ClPhe$^2$-D3Pal$^3$-Ser$^4$-NMeTyr$^5$-DLys(N-epsilon-Gly-Morpholinocarbonyl)$^6$-Leu$^7$-Lys(N-epsilon-isopropyl)$^8$-Pro$^9$-DAla$^{10}$NH$_2$ The procedure described in Example 23 is used but substituting morpholine for nicotinic hydrazide, after work-up, purification and lyophilization NAc-D2Nal$^1$-D4ClPhe$^2$-D3Pal$^3$-Ser$^4$-NMeTyr$^5$-DLys(N-epsilon-Gly-Morpholinocarbonyl)$^6$-Leu$^7$-Lys(N-epsilon-Isopropyl)$^8$-Pro$^9$-DAla$^{10}$NH$_2$ is obtained.

EXAMPLE 34

The procedure described in Example 33 is used but substituting the appropriate amines for morpholine, after work-up, purification and lyophilization the following compounds are obtained:

(a) NAc-D2Nal$^1$-D4ClPhe$^2$-D3Pal$^3$-Ser$^4$-NMeTyr-DLys[N-epsilon-Gly-N'-Me-Piperazinecarbonyl]$^6$-Leu$^7$-Lys(N-epsilon-Isopropyl)$^8$-Pro$^9$-DAla$^{10}$NH$_2$ (b) NAc-D2Nal$^1$-D4ClPhe$^2$-D3Pal$^3$-Ser$^4$-NMeTyr$^5$-DLys[N-epsilon-Gly-Pyrrolidinecarbonyl]$^6$-Leu$^7$-Lys(N-epsilon-Isopropyl)$^8$-Pro$^9$-DAla$^{10}$NH$_2$ (c) NAc-D2Nal$^1$-D4ClPhe$^2$-D3Pal$^3$-Ser$^4$-NMeTyr$^5$-DLys[N-epsilon-Gly-Piperidinecarbonyl]$^6$-Leu$^7$-Lys(N-epsilon-Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys[N-epsilon-Gly-Diethylaminocarbonyl]$^6$-Leu$^7$-Lys(N-epsilon-Isopropyl)$^8$-Pro$^9$-DAla$^{10}$NH$_2$ (e) NAc-D2Nal$^1$-D4ClPhe$^2$-D3Pal$^3$-Ser$^4$-NMeTyr$^5$-DLys[N-epsilon-Gly-Dipropylaminocarbonyl]$^6$-Leu$^7$-Lys(N-epsilon-Isopropyl)$^8$-Pro$^9$-DAla$^{10}$NH$_2$ (f) NAc-D2Nal$^1$-D4ClPhe$^2$-D3Pal$^3$-Ser$^4$-NMeTyr$^5$-DLys[N-epsilon-Gly-Diisopropylaminocarbonyl]$^6$-Leu$^7$-Lys(N-epsilon-Isopropyl)$^8$-Pro$^9$-DAla$^{10}$NH$_2$ (g) NAc-D2Nal$^1$-D4ClPhe$^2$-D3Pal$^3$-Ser$^4$-NMeTyr$^5$-DLys[N-epsilon-Gly-Phenethylaminocarbonyl]$^6$-Leu$^7$-Lys(N-epsilon-Isopropyl)$^8$-Pro$^9$-DAla$^{10}$NH$_2$ (h) NAc-D2Nal$^1$-D4ClPhe$^2$-D3Pal$^3$-Ser$^4$-NMeTyr$^5$-DLys[N-epsilon-Gly-3-Pyridine3-aminocarbonyl]$^6$-Leu$^7$-Lys(N-epsilon-Isopropyl)$^8$-Pro$^9$-DAla$^{10}$NH$_2$ (i) NAc-D2Nal$^1$-D4ClPhe$^2$-D3Pal$^3$-Ser$^4$-NMeTyr$^5$-DLys[N-epsilon-Gly-Pyridine-3-methylaminocarbonyl]$^6$-Leu$^7$-Lys(N-epsilon-Isopropyl)$^8$-Pro$^9$-DAla$^{10}$NH$_2$

EXAMPLE 35

The procedure described in Example 1 is used but substituting the appropriate acids for nicotinic acid, after work-up, purification and lyophilization the following compounds are obtained:

(a) NAc-D2Nal$^1$-D4ClPhe$^2$-D3Pal$^3$-Ser$^4$-NMeTyr$^5$-DLys(N-epsilon-Gly-Picolinyl)-Leu-Lys(N-epsilon-Isopropyl)-Pro-DAlaNH$_2$.

(b) NAc-D2Nal$^1$-D4ClPhe$^2$-D3Pal$^3$-Ser$^4$-NMeTyr$^5$-DLys(N-epsilon-Gly-isonicotinyl)$^6$-Leu$^7$-Lys(N-epsilon-isopropyl)$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys(N-epsilon-Gly-3-Indoleacetyl)$^6$-Leu$^7$-Lys(N-epsilon-Isopropyl)$^8$-Pro$^9$-DAla$^{10}$NH$_2$.

(d) NAc-D2Nal$^1$-D4ClPhe$^2$-D3Pal$^3$-Ser$^4$-NMeTyr$^5$-DLys(N-epsilon-Gly-Shikimyl)$^6$-Leu$^7$-Lys(N-epsilon-Isopropyl)$^8$-Pro$^9$-DAla$^{10}$NH$_2$.

(e) NAc-D2Nal$^1$-D4ClPhe$^2$-D3Pal$^3$-Ser$^4$-NMeTyr$^5$-DLys(N-epsilon-Gly-3-Quinolinyl)$^6$-Leu$^7$-Lys(N-epsilon-Isopropyl)$^8$-Pro$^9$-DAla$^{10}$NH$_2$.

(f) NAc-D2Nal$^1$-D4ClPhe$^2$-D3Pal$^3$-Ser$^4$-NMeTyr$^5$-DLys(N-epsilon-Gly-2-Pyrrolecarbonyl)$^6$-Leu$^7$-Lys(N-epsilon-Isopropyl)$^8$-Pro$^9$-DAla$^{10}$NH$_2$.

(g) NAc-D2Nal$^1$-D4ClPhe$^2$-D3Pal$^3$-Ser$^4$-NMeTyr$^5$-DLys(N-epsilon-Gly-Benzoyl)$^6$-Leu$^7$-Lys(N-epsilon-isopropyl)$^8$-Pro$^9$-DAla$^{10}$NH$_2$.

(h) NAc-D2Nal$^1$-D4ClPhe$^2$-D3Pal$^3$-Ser$^4$-NMeTyr$^5$-DLys(N-epsilon-Gly-p-MeO-Benzoyl)$^6$-Leu$^7$-Lys(N-epsilon-Isopropyl)$^8$-Pro$^9$-DAla$^{10}$NH$_2$.

(i) NAc-D2Nal$^1$-D4ClPhe$^2$-D3Pal$^3$-Ser$^4$-NMeTyr$^5$-DLys(N-epsilon-Gly-6-OH-Nicotinyl)$^6$-Leu$^7$-Lys(N-epsilon-Isopropyl)$^8$-Pro$^9$-DAla$^{10}$NH$_2$.

(j) NAc-D2Nal$^1$-D4ClPhe$^2$-D3Pal$^3$-Ser$^4$-NMeTyr$^5$-DLys (N-epsilon-Gly-2-OH-Nicotinyl)$^6$-Leu$^7$-Lys(N-epsilon-Isopropyl)$^8$-Pro$^9$-DAla$^{10}$NH$_2$.

(k) NAc-D2Nal$^1$-D4ClPhe$^2$-D3Pal$^3$-Ser$^4$-NMeTyr$^5$-DLys (N-epsilon-Gly-3-Furoyl)$^6$-Leu$^7$-Lys(N-epsilon-isopropyl)$^8$-Pro$^9$-DAla$^{10}$NH$_2$.

(l) NAc-D2Nal$^1$-D4ClPhe$^2$-D3Pal$^3$-Ser$^4$-NMeTyr$^5$-DLys (N-epsilon-Gly-2-Naphthoyl)$^6$-Leu$^7$-Lys(N-epsilon-Isopropyl)$^8$-Pro$^9$-DAla$^{10}$NH$_2$.

(m) NAc-D2Nal$^1$-D4ClPhe$^2$-D3Pal$^3$-Ser$^4$-NMeTyr$^5$-DLys (N-epsilon-Gly-Dihydroshikimyl)$^6$-Leu$^7$-Lys(N-epsilon-isopropyl)$^8$-Pro$^9$-DAla$^{10}$NH$_2$.

(n) NAc-D2Nal$^1$-D4ClPhe$^2$-D3Pal$^3$-Ser$^4$-NMeTyr$^5$-DLys (N-epsilon-Gly-Propionyl)$^6$-Leu$^7$-Lys(N-epsilon-Isopropyl)$^8$-Pro$^9$-DAla$^{10}$NH$_2$.

(o) NAc-D2Nal$^1$-D4ClPhe$^2$-D3Pal$^3$-Ser$^4$-NMeTyr$^5$-DLys (N-epsilon-Gly-6-Methylnicotinyl)$^6$-Leu$^7$-Lys(N-epsilon-Isopropyl)$^8$-Pro$^9$-DAla$^{10}$NH$_2$.

(p) NAc-D2Nal$^1$-D4ClPhe$^2$-D3Pal$^3$-Ser$^4$-NMeTyr$^5$-DLys (N-epsilon-Gly-2-Methylnicotinyl)$^6$-Leu$^7$-Lys(N-epsilon-Isopropyl)$^8$-Pro$^9$-DAla$^{10}$NH$_2$.

(q) NAc-D2Nal$^1$-D4ClPhe$^2$-D3Pal$^3$-Ser$^4$-NMeTyr$^5$-DLys (N-epsilon-Gly-Pyrazine-2-carbonyl)$^6$-Leu$^7$-Lys(N-epsilon-Isopropyl)$^8$-Pro$^9$-DAla$^{10}$NH$_2$.

(r) NAc-D2Nal$^1$-D4ClPhe$^2$-D3Pal$^3$-Ser$^4$-NMeTyr$^5$-DLys (N-epsilon-Gly-6-Chloronicotinyl)$^6$-Leu$^7$-Lys(N-epsilon-Isopropyl)$^8$-Pro$^9$-DAla$^{10}$NH$_2$.

(s) NAc-D2Nal$^1$-D4ClPhe$^2$-D3Pal$^3$-Ser$^4$-NMeTyr$^5$-DLys (N-epsilon-Gly-Salicyl)$^6$-Leu$^7$-Lys(N-epsilon-Isopropyl)$^8$-Pro$^9$-DAla$^{10}$NH$_2$.

(t) NAc-D2Nal$^1$-D4ClPhe$^2$-D3Pal$^3$-Ser$^4$-NMeTyr$^5$-DLys (N-epsilon-Gly-Benzofuran-2-carbonyl)$^6$-Leu$^7$-Lys (N-epsilon-Isopropyl)$^8$-Pro$^9$-DAla$^{10}$NH$_2$.

EXAMPLE 36

NAc-D2Nal$^1$-D4ClPhe$^2$-D3Pal$^3$-Ser$^4$-NMeTyr$^5$-DLys[N-epsilon-(N'-Carbonyl-Diaminoethane-N''-Furoyl)]$^6$-Leu$^7$-Arg$^8$-Pro$^9$-DAla$^{10}$NH$_2$ The procedure described in Example 14 is used but substituting 2-furoic acid for nicotinic acid. After work-up, lyophilization, and HPLC purification NAc-D2Nal$^1$-D4ClPhe$^2$-D3Pal$^3$-Ser$^4$-NMeTyr$^5$-DLys[N-epsilon-(N'-Carbonyl-Diaminoethane-N''-Furoyl)]$^6$-Leu$^7$-Arg$^8$-Pro$^9$-DAla$^{10}$NH$_2$ is obtained as the trifluoroacetate salt.

EXAMPLE 37

The same procedure described in Example 2 but substituting BOC-Arg(Tos) for BOC-Lys(N-epsilon-Cbz, Isopropy) and substituting the appropriate acid hydrazizes for 2-furoic hydrazides. After work-up, HPLC purification, and lyophilization the following compounds are obtained:

(a) NAc-D2Nal$^1$-D4ClPhe$^2$-D3Pal$^3$-Ser$^4$-NMeTyr$^5$-DLys (N-epsilon-Azagly-2-Furoyl)$^6$-Leu$^7$-Arg$^8$-Pro$^9$-DAla$^{10}$NH$_2$; R$_t$=41.40 min; FAB Mass spec. m/e 1568 (M+H)$^+$. Amino Acid Analysis: 1.02 Ala; 1.04 Pro; 0.99 Arg; 1.01 Leu; 0.93 Lys; 1.03 NMeTyr; 0.53 Ser; 1.01 3Pal; 1.01 4ClPhe.

(b) NAc-D2Nal$^1$-D4ClPhe$^2$-D3Pal$^3$-Ser$^4$-NMeTyr$^5$-DLys (N-epsilon-Azagly-Nicotinyl)$^6$-Leu$^7$-Arg$^8$-Pro$^9$-DAla$^{10}$NH$_2$; R$_t$=38.15 min; FAB Mass spec. m/e 1580 (M+H)$^+$. Amino Acid Analysis: 1.01 Ala; 1.01 Pro; 0.98 Arg; 1.01 Leu; 0.99 Lys; 1.02 NMeTyr; 0.54 Ser; 1.01 3Pal; 1.09 4ClPhe.

(c) NAc-D2Nal$^1$-D4ClPhe$^2$-D3Pal$^3$-Ser$^4$-NMeTyr$^5$-DLys (N-epsilon-Azagly-Shikimyl)$^6$-Leu$^7$-Arg$^8$-Pro$^9$-DAla$^{10}$NH$_2$.

EXAMPLE 38

Using the procedure described in Example 11 but substituting the appropriate BOC-amino acids for BOC-DSer, after work-up, HPLC purification and lyophilization the following compounds are obtained as the trifluoroacetate salt:

(a) NAc-D2Nal$^1$-D4ClPhe$^2$-D3Pal$^3$-Ser$^4$-NMeTyr$^5$-DLys (N-epsilon-DAla-Shikimyl)$^6$-Leu$^7$-Arg$^8$-Pro$^9$-DAla$^{10}$NH$_2$; R$_t$=17.05 min; FAB Mass spec. m/e 1642 (M+H)$^+$. Amino Acid Anal: 2.01 Ala; 1.01 Pro; 0.96 Arg; 1.02 Leu; 0.99 Lys; 1.14 NMeTyr; 0.56 Ser; 0.94 3Pal; 1.02 4ClPhe.

(c) NAc-D2Nal$^1$-D4ClPhe$^2$-D3Pal$^3$-Ser$^4$-NMeTyr$^5$-DLys (N-epsilon-Sar-Shikimyl)$^6$-Leu$^7$-Arg$^8$-Pro$^9$-DAla$^{10}$NH$_2$ (d) NAc-D2Nal$^1$-D4ClPhe$^2$-D3Pal$^3$-Ser$^4$-NMeTyr$^5$-DLys (N-epsilon-DThr-Shikimyl)$^6$-Leu$^7$-Arg$^8$-Pro$^9$-DAla$^{10}$NH$_2$; R$_t$=21.90 min; FAB Mass spec. m/e 1672 (M+H)$^+$. Amino Acid Anal: 1.01 Ala; 0.99 Pro; 0.96 Arg; 1.02 Leu; 1.02 Lys; 1.12 NMeTyr; 0.53 Ser; 0.94 3Pal; 1.024ClPhe; 0.77 Thr.

(e) NAc-D2Nal$^1$-D4ClPhe$^2$-D3Pal$^3$-Ser$^4$-NMeTyr$^5$-DLys (N-epsilon-DHis-Shikimyl)$^6$-Leu$^7$-Arg$^8$-Pro$^9$-DAla$^{10}$NH$_2$; R$_t$=15.10 min; FAB Mass spec. m/e 1708 (M+H)$^+$. Amino Acid Anal: 1.02 Ala; 1.01 Pro; 0.96 Arg; 1.02 Leu; 1.02 Lys; 1.13 NMeTyr; 0.52 Ser; 0.95 3Pal; 1.02 4ClPhe; 0.97 His.

(f) NAc-D2Nal$^1$-D4ClPhe$^2$-D3Pal$^3$-Ser$^4$-NMeTyr$^5$-DLys (N-epsilon-D3Pal-Shikimyl)$^6$-Leu$^7$-Arg$^8$-Pro$^9$-DAla$^{10}$NH$_2$; R$_t$=13.65 min; FAB Mass spec. m/e 1719 (M+H)$^+$. Amino Acid Anal: 1.00 Ala; 1.02 Pro; 0.95 Arg; 1.02 Leu; 1.00 Lys; 1.14 NMeTyr; 0.53 Ser; 1.86 3Pal; 1.02 4ClPhe.

EXAMPLE 39

Using the procedure described in Example 30 but substituting BOC-Orn(FMOC) for BOC-DLys(FMOC) and substituting the appropriate acids, after work-up, HPLC purification and lyophilization the following compounds are obtained as the trifluoroacetate salt:

(a) NAc-D2Nal$^1$-D4ClPhe$^2$-D3Pal$^3$-Ser$^4$-NMeTyr$^5$-DOrn (N-epsilon-Gly-Shikimyl)$^6$-Leu$^7$-Arg$^8$-Pro$^9$-DAla$^{10}$NH$_2$ (b) NAc-D2Nal$^1$-D4ClPhe$^2$-D3Pal$^3$-Ser$^4$-NMeTyr$^5$-DOrn (N-epsilon-DSer-Shikimyl)$^6$-Leu$^7$-Arg$^8$-Pro$^9$-DAla$^{10}$NH$_2$ (c) NAc-D2Nal$^1$-D4ClPhe$^2$-D3Pal$^3$-Ser$^4$-NMeTyr$^5$-DOrn (N-epsilon-Gly-Nicotinyl)$^6$-Leu$^7$-Arg$^8$-Pro$^9$-DAla$^{10}$NH$_2$ (d) NAc-D2Nal$^1$-D4ClPhe$^2$-D3Pal$^3$-Ser$^4$-NMeTyr$^5$-DOrn (N-epsilon-DSer-Nicotinyl)$^6$-Leu$^7$-Arg$^8$-Pro$^9$-DAla$^{10}$NH$_2$

EXAMPLE 40

NAc-D2Nal$^1$-D4ClPhe$^2$-D3Pal$^3$-Ser$^4$-NMeTyr$^5$-DLys(N-epsilon-(Beta-alanyl)2-Furoyl)$^6$-Leu$^7$-Lys(N-epsilon-isopropyl)$^8$-Pro$^9$-DAla$^{10}$NH$_2$.

The procedure described in Example 1 was used but substituting BOC-Beta-alanine for BOC-Gly. After work-up, HPLC purification and lyophilization NAc-D2Nal-D4ClPhe-D3Pal-Ser-NMeTyr-DLys(N-epsilon-(Beta-alanyl)2-Furoyl)-Leu-Lys(N-epsilon-Isopropyl)-Pro-DAlaNH$_2$ was obtained as the trifluoroacetate salt; R$_t$=26.56 min; FAB Mass spec. m/e 1594 (M+H)$^+$. Amino Acid Analysis: 1.02 Ala; 1.00 Pro; 0.90 Lys(Isp); 1.00 Leu; 0.98 Lys; 1.11 NMeTyr; 0.60 Ser; 1.04 3Pal; 1.03 4ClPhe.

EXAMPLE 41

NAc-D2Nal$^1$-D4ClPhe$^2$-D3Pal$^3$-Ser$^4$-NMeTyr$^5$-DLys[N-epsilon-(N'-Carbonyl-Piperazine-N''-2-Furoyl)]$^6$-Leu$^7$-Lys (N-epsilon-Isopropyl)$^8$-Pro$^9$-DAla$^{10}$NH$_2$.

The procedure described in Example 14 was used but substituting piperazine for ethylenediamine, 2-furoic acid for nicotinic acid and BOC-Lys(N,N-epsilon-Isp,Cbz) for BOC-Arg(Tos). After work-up, HPLC purification and lyophilization NAc-D2Nal-D4ClPhe-D3Pal-Ser-NMeTyr-DLys[N-epsilon-(N'-Carbonyl-Piperazine-N"-2-Furoyl)]-Leu-Lys(N-epsilon-Isopropyl)-Pro-DAlaNH$_2$ was obtained as the trifluoroacetate salt; R$_t$=26.39 min; FAB Mass spec. m/e 1749 (M+H)$^+$. Amino Acid Analysis: 1.04 Ala; 0.97 Pro; 0.96 Lys(Isp); 0.99 Leu; 0.99 Lys; 1.11 NMeTyr; 0.54 Ser; 1.10 3Pal; 1.01 4ClPhe.

EXAMPLE 42

NAc-D2Nal$^1$-D4ClPhe$^2$-D3Pal$^3$-Ser$^4$-NMeTyr$^5$-DLys[N-epsilon-(N'-Carbonyl-Diaminopropane-N"-Shikimyl)]$^6$-Leu$^7$-Arg$^8$-Pro$^9$-DAla$^{10}$NH$_2$.

The procedure described in Example 15 was used but substituting 1,3-diaminopropane for ethylenediamine, 2-furoic acid for nicotinic acid and BOC-Lys(N,N-epsilon-Isp,Cbz) for BOC-Arg(Tos). After work-up, HPLC purification and lyophilization NAc-D2Nal-D4ClPhe-D3Pal-Ser-NMeTyr-DLys[N-epsilon-(N'-Carbonyl-Diaminopropane-N"-Shikimyl)]-Leu-Arg-Pro-DAlaNH$_2$ was obtained as the trifluoroacetate salt; R$_t$=28.23 min; FAB Mass spec. m/e 1671 (M+H)$^+$. Amino Acid Analysis: 1.04 Ala; 1.00 Pro; 0.96 Arg; 1.01 Leu; 0.98 Lys; 0.89 NMeTyr; 0.51 Ser; 1.10 3Pal; 1.018 4ClPhe.

EXAMPLE 43

NAc-D2Nal$^1$-D4ClPhe$^2$-D3Pal$^3$-Ser$^4$-NMeTyr$^5$-DLys(N-epsilon-5-Aminovaleryl-Nicotinyl)$^6$-Leu$^7$-Lys(N-epsilon-Isopropyl)$^8$-Pro$^9$-DAla$^{10}$NH$_2$.

The procedure described in Example 1 was used but substituting BOC-5-aminovaleric acid for BOC-Gly. After work-up, HPLC purification and lyophilization NAc-D2Nal-D4ClPhe-D3Pal-Ser-NMeTyr-DLys(N-epsilon-5-Aminovaleryl-Nicotinyl)-Leu-Lys(Isp)-Pro-DAlaNH$_2$ was obtained as the trifluoroacetate salt; R$_t$=21.33 min; FAB Mass spec. m/e 1633 (M+H)$^+$. Amino Acid Analysis: 1.00 Ala; 1.01 Pro; 0.91 Lys(Isp); 0.98 Leu; 1.01 Lys; 0.91 NMeTyr; 0.54 Ser; 1.0.6 3Pal; 0.95 4ClPhe.

EXAMPLE 44

NAc-D2Nal$^1$-D4ClPhe$^2$-D3Pal$^3$-Ser$^4$-NMeTyr$^5$-DLys(N-epsilon-7-Aminoheptanoyl-Nicotinyl)$^6$-Leu$^7$-Lys(N-epsilon-Isopropyl)$^8$-Pro$^9$-DAla$^{10}$NH$_2$.

The procedure described in Example 1 was used but substituting BOC-7-heptanoic acid for BOC-Gly. After work-up, HPLC purification and lyophilization NAc-D2Nal-D4ClPhe-D3Pal-Ser-NMeTyr-DLys(N-epsilon-7-Aminoheptanoyl-Nicotinyl)-Leu-Lys(Isp)-Pro-DAlaNH$_2$ was obtained as the trifluoroacetate salt; R$_t$=18.64 min; FAB Mass spec. m/e 1661 (M+H)$^+$. Amino Acid Analysis: 1.04 Ala; 1.02 Pro; 0.92 Lys(Isp); 1.00 Leu; 0.94 Lys; 1.01 NMeTyr; 0.42 Ser; 0.95 3Pal; 0.98 4ClPhe.

EXAMPLE 45

NAc-D2Nal$^1$-D4ClPhe$^2$-D3Pal$^3$-Ser$^4$-NMePhe(Atz)$^5$-DLys(N-epsilon-Gly-Nicotinyl)$^6$-Leu$^7$-Lys(N-epsilon-Isopropyl)$^8$-Pro$^9$-DAla$^{10}$NH$_2$.

The solid phase synthesis protocol outlined in Exmple 1 was halted after the coupling of BOC-DLys(FMOC) to yield the BOC-DLys(FMOC)-Leu-Lys(Isp,CBZ)-Pro-DAlaNH-resin. The resin was treated for 2 h with 30% piperidine/DMF (20 mL) to remove the FMOC protecting group. FMOC-Gly was coupled using the standard two-2 hr coupling protocol and reagents as described in Example 1. No deblocking steps were used however and the FMOC group was removed by treatment for 2 hours with 30% piperidine/DMF (20 mL), leaving the BOC group intact on the alpha-amine of the DLys. Nicotinic acid was also coupled by standard protocol (two-2 hr, again with no deblocking) and then the resin was continued by the standard BOC protocols. BOC-NMePhe(4-N-FMOC) was coupled in place of BOC-NMeTyr(O-2,6-ClBzl). Upon completion of the synthetic protocol NAc-D2Nal-D4ClPhe-D3Pal-Ser-NMePhe(FMOC)-DLys(Gly-Nic)-Leu-Lys(Isp,Cbz)-Pro-DAlaNH-resin was obtained. The resin was again treated for 2 h with 30% piperidine/DMF (20 mL) to remove the FMOC protecting group. The resin was washed three times each with (1:1) DCM/DMF and DCM, then treated with a solution of diphenyl cyanocarbonimidate (0.43 g) in DMF (15 mL), and the mixture bubbled for 16 h. The resin was washed three times each with (1:1) DCM/DMF, MeOH, and DCM, then treated with hydrazine (10 mL) for 8 hours. The resin was again washed three times each with (1:1) DCM/DMF, MeOH, and DCM, and dried in vacuo overnight over P$_2$O$_5$. After cleavage of the peptide with HF and HPLC purification NAc-D2Nal-D4ClPhe-D3Pal-Ser-NMePhe(Atz)-DLys(Azagly-Nicotinyl)-Leu-Lys(Isp)-Pro-DAlaNH$_2$ was obtained as the trifluoroacetate salt; R$_t$=13.80 min; FAB Mass spec. m/e 1672 (M+H)$^+$. Amino Acid Anal: 1.00 Ala; 0.98 Pro; 1.06 Lys(Isp); 1.02 Leu; 0.98 Lys; 1.02 Gly; 0.56 Ser; 1.00 3Pal; 1.10 4ClPhe.

EXAMPLE 46

NAc-D2Nal$^1$-D4ClPhe$^2$-D3Pal$^3$-Ser$^4$-NMePhe(Atz)$^5$-DLys(N-epsilon-Azagly-Nicotinyl)$^6$-Leu$^7$-Lys(N-epsilon-Isopropyl)$^8$-Pro$^9$-DAla$^{10}$NH$_2$.

The same procedure outlined in Example 45 was used, but replacing the FMOC-Gly and nicotinic acid couplings by treated with a solution of 1,1'-carbonyldiimidazole (0.59 g) in DMF/DCM (20 mL) and the mixture bubbled for 1 h. The resin was washed three times each with (1:1) DCM/DMF, and DCM, then treated with nicotinic hydrazide (0.48 g) in (1:1) DCM/DMF (20 mL) and the mixture bubbled for 18 h. The resin was again washed three times each with (1:1) DCM/DMF, and DCM, and the rest of the peptide was synthesized as in Example 45. After HF treatment and HPLC purification NAc-D2Nal-D4ClPhe-D3Pal-Ser-NMePhe(Atz)-DLys(N-epsilon-Azagly-Nicotinyl)-Leu-Lys(Isp)-Pro-DAlaNH$_2$ was obtained as the trifluoroacetate salt; R$_t$=14.43 min; FAB Mass spec. m/e 1674 (M+H)$^+$. Amino Acid Anal: 1.02 Ala; 0.99 Pro; 1.01 Lys(Isp); 1.00 Leu; 0.99 Lys; 0.4 Ser; 0.97 3Pal; 1.05 4ClPhe.

EXAMPLE 47

NAc-D2Nal$^1$-D4ClPhe$^2$-D3Pal$^3$-Ser$^4$-NMePhe(Atz)$^5$-DLys(N-epsilon-Azagly-2-Furoyl)$^6$-Leu$^7$-Lys(N-epsilon-isopropyl)$^8$-Pro$^9$-DAla$^{10}$NH$_2$. The same procedure outlined in Example 46 was used, but substituting 2-furoic hydrazide for nicotinic hydrazide. After cleavage of the peptide from the resin with HF and HPLC purification NAc-D2Nal-D4ClPhe-D3Pal-Ser-NMePhe(Atz)-DLys(N-epsilon-Azagly-2-Furoyl)-Leu-Lys(Isp)-Pro-DAlaNH$_2$ was obtained as the trifluorocetate salt; R$_t$=16.72 min; FAB Mass spec. m/e 1662 (M+H)$^+$. Amino Acid Anal: 1.02 Ala; 0.99 Pro; 1.14 Lys(Isp); 1.03 Leu; 0.96 Lys; 0.60 Ser; 1.05 3Pal; 1.17 4ClPhe.

EXAMPLE 48

The protocol described in Example 17 was used but substituting the appropriate protected amino acids and acids in place of BOC-Gly and shikimic acids. After cleavage of the peptide from the resin with HF, work-up, HPLC purification and lyphilization the following peptides were obtained as trifluoroacetate salts:

(a) NAc-D2Nal$^1$-D4ClPhe$^2$-D3Pal$^3$-Ser$^4$-NMeTyr$^5$-DLys(N-epsilon-Gly-Picolinyl)$^6$-Leu$^7$-Arg$^8$-Pro$^9$-DAla$^{10}$NH$_2$; R$_t$=42.70 min; FAB Mass spec. m/e 1577 (M+H)$^+$. Amino Acid Anal: 1.01 Ala; 0.98 Pro; 0.96 Arg; 1.03 Leu; 0.99 Lys; 1.07 NMeTyr; 0.52 Ser; 0.94 3Pal; 1.02 4ClPhe.

(b) NAc-D2Nal$^1$-D4ClPhe$^2$-D3Pal$^3$-Ser$^4$-NMeTyr$^5$-DLys(N-epsilon-D-Ser-Picolinyl)$^6$-Leu$^7$-Arg$^8$-Pro$^9$-DAla$^{10}$NH$_2$; R$_t$=20.60 min; FAB Mass spec. m/e 1607 (M+H)$^+$. Amino Acid Anal: 1.01 Ala; 1.00 Pro; 0.98 Arg; 1.04 Leu; 0.97 Lys; 1.14 NMeTyr; 1.00 Ser; 0.95 3Pal; 1.04 4ClPhe.

(c) NAc-D2Nal$^1$-D4ClPhe$^2$-D3Pal$^3$-Ser$^4$-NMeTyr$^5$-DLys(N-epsilon-D-Thr-Shikimyl)$^6$-Leu$^7$-Arg$^8$-Pro$^9$-DAla$^{10}$NH$_2$; R$_t$=38.00 min; FAB Mass spec. m/e 1672 (M+H)$^+$. Amino Acid Anal: 1.01 Ala; 0.99 Pro; 0.96 Arg; 1.02 Leu; 1.02 Lys; 1.12 NMeTyr; 0.53 Ser; 0.94 3Pal; 1.02 4ClPhe.

(d) NAc-D2Nal$^1$-D4ClPhe$^2$-D3Pal$^3$-Ser$^4$-NMeTyr$^5$-DLys(N-epsilon-D-Ala-Shikimyl)$^6$-Leu$^7$-Arg$^8$-Pro$^9$-DAla$^{10}$NH$_2$; R$_t$=38.35 min; FAB Mass spec. m/e 1642 (M+H)$^+$. Amino Acid Anal: 2.01 Ala; 1.01 Pro; 0.96 Arg; 1.02 Leu; 0.99 Lys; 1.15 NMeTyr; 0.56 Ser; 0.94 3Pal; 1.02 4ClPhe.

(e) NAc-D2Nal$^1$-D4ClPhe$^2$-D3Pal$^3$-Ser$^4$-NMeTyr$^5$-DLys(N-epsilon-Ala-Shikimyl)$^6$-Leu$^7$-Arg$^8$-Pro$^9$-DAla$^{10}$NH$_2$; R$_t$=38.25 min; FAB Mass spec. m/e 1642 (M+H)$^+$. Amino Acid Anal: 2.00 Ala; 1.01 Pro; 0.95 Arg; 1.01 Leu; 1.02 Lys; 1.14 NMeTyr; 0.51Ser; 0.93 3Pal; 1.03 4ClPhe.

(f) NAc-D2Nal$^1$-D4ClPhe$^2$-D3Pal$^3$-Ser$^4$-NMeTyr$^5$-DLys(N-epsilon-Sar-Shikimyl)$^6$-Leu$^7$-Arg$^8$-Pro$^9$-DAla$^{10}$NH$_2$; R$_t$=38.20 min; FAB Mass spec. m/e 1642 (M+H)$^+$. Amino Acid Anal: 1.01 Ala; 0.99 Pro; 0.96 Arg; 1.03 Leu; 1.01 Lys; 1.20 NMeTyr; 0.58 Ser; 0.95 3Pal; 1.03 4ClPhe.

(g) NAc-D2Nal$^1$-D4ClPhe$^2$-D3Pal$^3$-Ser$^4$-NMeTyr$^5$-DLys(N-epsilon-Beta-alanyl-Shikimyl)$^6$-Leu$^7$-Arg$^8$-Pro$^9$-DAla$^{10}$NH$_2$; R$_t$=37.80 min; FAB Mass spec. m/e 1642 (M+H)$^+$. Amino Acid Anal: 1.03Ala; 1.02 Pro; 0.97 Arg; 1.05 Leu; 0.92 Lys; 0.88 NMeTyr; 0.61 Ser; 0.97 3Pal; 1.02 4ClPhe.

(h) NAc-D2Nal$^1$-D4ClPhe$^2$-D3Pal$^3$-Ser$^4$-NMeTyr$^5$-DLys(N-epsilon-D-His-Shikimyl)$^6$-Leu$^7$-Arg$^8$-Pro$^9$-DAla$^{10}$NH$_2$; R$_t$=15.90 min; FAB Mass spec. m/e 1708 (M+H)$^+$. Amino Acid Anal: 1.02 Ala; 1.01 Pro; 0.96 Arg; 1.02 Leu; 1.02 Lys; 0.97 His; 1.10 NMeTyr; 0.52 Ser; 0.95 3Pal; 1.02 4ClPhe.

(i) NAc-D2Nal$^1$-D4ClPhe$^2$-D3Pal$^3$-Ser$^4$-NMeTyr$^5$-DLys(N-epsilon-D-3Pal-Shikimyl)$^6$-Leu$^7$-Arg$^8$-Pro$^9$-DAla$^{10}$NH$_2$; R$_t$=15.95 min; FAB Mass spec. m/e 1719 (M+H)$^+$. Amino Acid Anal: 1.00 Ala; 1.02 Pro; 0.95 Arg; 1.02 Leu; 1.00 Lys; 1.14 NMeTyr; 0.53 Ser; 1.86 3Pal; 1.02 4ClPhe.

(j) NAc-D2Nal$^1$-D4ClPhe$^2$-D3Pal$^3$-Ser$^4$-NMeTyr$^5$-DLys(N-epsilon-D-Ser-Gly-Shikimyl)$^6$-Leu$^7$-Arg$^8$-Pro$^9$-DAla$^{10}$NH$_2$; R$_t$=21.30 min; FAB Mass spec. m/e 1715 (M+H)$^+$. Amino Acid Anal: 1.01 Ala; 0.99 Pro; 0.95 Arg; 1.02 Leu; 0.98 Lys; 1.04 Gly; 1.13 NMeTyr; 1.04 Ser; 0.95 3Pal; 1.03 4ClPhe.

(k) NAc-D2Nal$^1$-D4ClPhe$^2$-D3Pal$^3$-Ser$^4$-NMeTyr$^5$-DLys(N-epsilon-D-Ser-Gly-Nicotinyl)$^6$-Leu$^7$-Arg$^8$-Pro$^9$-DAla$^{10}$NH$_2$; R$_t$=16.08 min; FAB Mass spec. m/e 1664 (M+H)$^+$. Amino Acid Anal: 1.01 Ala; 1.00 Pro; 0.96 Arg; 1.03 Leu; 0.98 Lys; 1.01 Gly; 1.17 NMeTyr; 1.05 Ser; 0.96 3Pal; 1.04 4ClPhe.

EXAMPLE 49

The protocol described in Example 17 was used but substituting BOC-DOrn(FMOC) for BOC-DLys(FMOC) and subtituting the appropriate protected amino acids and acids in place of BOC-Gly and shikimic acids. After cleavage of the peptide from the resin with HF, work-up, HPLC purification and lyphilization the following peptides were obtained as trifluoroacetate salts:

(a) NAc-D2Nal$^1$-D4ClPhe$^2$-D3Pal$^3$-Ser$^4$-NMeTyr$^5$-DOrn(N-epsilon-Gly-Nicotinyl)$^6$-Leu$^7$-Arg$^8$-Pro$^9$-DAla$^{10}$NH$_2$; R$_t$=16.80 min; FAB Mass spec. m/e 1563 (M+H)$^+$. Amino Acid Anal: 1.01 Ala; 0.99 Pro; 0.97 Arg; 1.03 Leu; 1.01 Orn; 0.98 Gly; 1.07 NMeTyr; 0.46 Ser; 0.96 3Pal; 1.04 4ClPhe.

(b) NAc-D2Nal$^1$-D4ClPhe$^2$-D3Pal$^3$-Ser$^4$-NMeTyr$^5$-DOrn(N-epsilon-DSer-Nicotinyl)$^6$-Leu$^7$-Arg$^8$-Pro$^9$-DAla$^{10}$NH$_2$; R$_t$=16.95 min; FAB Mass spec. m/e 1563 (M+H)$^+$. Amino Acid Anal: 1.03 Ala; 1.00 Pro; 0.95 Arg; 1.02 Leu; 1.00 Orn; 0.99 NMeTyr; 0.99 Ser; 0.93 3Pal; 1.02 4ClPhe.

(c) NAc-D2Nal$^1$-D4ClPhe$^2$-D3Pal$^3$-Ser$^4$-NMeTyr$^5$-DOrn(N-epsilon-Gly-Shikimyl)$^6$-Leu$^7$-Arg$^8$-Pro$^9$-DAla$^{10}$NH$_2$; R$_t$=17.15 min; FAB Mass spec. m/e 1614 (M+H)$^+$. Amino Acid Anal: 1.02 Ala; 0.99Pro; 0.96 Arg; 1.03 Leu; 1.07 Orn; 1.08 NMeTyr; 1.02 Ser; 0.94 3Pal; 1.02 4ClPhe.

(d) NAc-D2Nal$^1$-D4ClPhe$^2$-D3Pal$^3$-Ser$^4$-NMeTyr$^5$-DOrn(N-epsilon-DSer-Shikimyl)$^6$-Leu$^7$-Arg$^8$-Pro$^9$-DAla$^{10}$NH$_2$; R$_t$=16.75 min; FAB Mass spec. m/e 1644 (M+H)$^+$. Amino Acid Anal: 1.01 Ala; 1.01 Pro; 0.96 Arg; 1.02 Leu; 1.01 Orn; 0.96 Gly; 1.11 NMeTyr; 0.47 Ser; 0.95 3Pal; 1.04 4ClPhe.

EXAMPLE 50

Using the procedure described in Example 11 but substituting appropriate acids and amino acids for shikimic acid, after work-up, HPLC purification, and lyophilization the following compounds are obtained as the trifluoroacetate:

(a) NAc-D2Nal$^1$-D4ClPhe$^2$-D3Pal$^3$-Ser$^4$-NMeTyr$^5$-DLys(N-epsilon-DSer-2-Furoyl)$^6$-Leu$^7$-Arg$^8$-Pro$^9$-DAla$^{10}$NH$_2$.

(b) NAc-D2Nal$^1$-D4ClPhe$^2$-D3Pal$^3$-Ser$^4$-NMeTyr$^5$-DLys(N-epsilon-DSer-Isonicotinyl)$^6$-Leu$^7$-Arg$^8$-Pro$^9$-DAla$^{10}$NH$_2$.

(c) NAc-D2Nal$^1$-D4ClPhe$^2$-D3Pal$^3$-Ser$^4$-NMeTyr$^5$-DLys(N-epsilon-DSer-3-Pyridineacetyl)$^6$-Leu$^7$-Arg$^8$-Pro$^9$-DAla$^{10}$NH$_2$.

(d) NAc-D2Nal$^1$-D4ClPhe$^2$-D3Pal$^3$-Ser$^4$-NMeTyr$^5$-DLys(N-epsilon-DSer-3-Quinolinyl)$^6$-Leu$^7$-Arg$^8$-Pro$^9$-DAla$^{10}$NH$_2$; R$_t$=18.85 win; FAB Mass spec. m/e 1658 (M+H)$^+$. Amino Acid Anal: 1.04 Ala; 0.99 Pro; 0.94 Arg; 1.01 Leu; 1.04 Lys; 1.34 NMeTyr; 0.99 Ser; 1.01 3Pal; 1.04 4ClPhe.

(e) NAc-D2Nal$^1$-D4ClPhe$^2$-D3Pal$^3$-Ser$^4$-NMeTyr$^5$-DLys(N-epsilon-DSer-4-Quinolinyl)$^6$-Leu$^7$-Arg$^8$-Pro$^9$-DAla$^{10}$NH$_2$; R$_t$=17.87 min; FAB Mass spec. m/e 1657 (M+H)$^+$. Amino Acid Anal: 1.03 Ala; 0.98 Pro; 0.97 Arg; 0.99 Leu; 1.05 Lys; 1.37 NMeTyr; 1.1 Ser; 0.96 3Pal; 0.99 4ClPhe.

(f) NAc-D2Nal$^1$-D4ClPhe$^2$-D3Pal$^3$-Ser$^4$-NMeTyr$^5$-DLys(N-epsilon-DSer-3-Tetrahydrofuryl)$^6$-Leu$^7$-Arg$^8$-Pro$^9$-DAla$^{10}$NH$_2$.

(g) NAc-D2Nal$^1$-D4ClPhe$^2$-D3Pal$^3$-Ser$^4$-NMeTyr$^5$-DLys(N-epsilon-DSer-2-Pyrazinecarbonyl)$^6$-Leu$^7$-Arg$^8$-Pro$^9$-DAla$^{10}$NH$_2$; R$_t$=19.40 win; FAB Mass spec. m/e 1608 (M+H)$^+$. Amino Acid Anal: 1.05 Ala; 1.01 Pro; 0.93 Arg; 1.01 Leu; 0.95 Lys; 1.11 NMeTyr; 0.94 Ser; 0.95 3Pal; 1.05 4ClPhe.

(h) NAc-D2Nal$^1$-D4ClPhe$^2$-D3Pal$^3$-Ser$^4$-NMeTyr$^5$-DLys
(N-epsilon-Gly-DSer-Shikimyl)$^6$-Leu$^7$-Arg$^8$-Pro$^9$-
DAla$^{10}$NH$_2$.

(i) NAc-D2Nal$^1$-D4ClPhe$^2$-D3Pal$^3$-Ser$^4$-NMeTyr$^5$-DLys
(N-epsilon-Gly-DSer-Nicotinyl)$^6$-Leu$^7$-Arg$^8$-Pro$^9$-
DAla$^{10}$NH$_2$.

EXAMPLE 51

Using the procedure described in Example 10 but substituting the appropriate acids for nicotinic acid, after work-up, lyophilization, and HPLC purification the following compounds are obtained as the trifluoroacetate salts:

(a) NAc-D2Nal$^1$-D4ClPhe$^2$-D3Pal$^3$-Ser$^4$-NMeTyr$^5$-DLys
(N-epsilon-Gly-3-Furoyl)$^6$-Leu$^7$-Arg$^8$-Pro$^9$-DAla$^{10}$-NH$_2$;
R$_t$=21.2 min; FAB Mass spec. m/e 1566 (M+H)$^+$. Amino
Acid Anal: 1.04 Ala; 1.00 Pro; 0.95 Arg; 1.01 Leu; 0.92
Lys; 1.02 Gly; 1.2 NMeTyr; 0.37 Ser; 0.95 3Pal; 1.05
4ClPhe.

(b) NAc-D2Nal$^1$-D4ClPhe$^2$-D3Pal$^3$-Ser$^4$-NMeTyr$^5$-DLys
(N-epsilon-Gly-Isonicotinyl)$^6$-Leu$^7$-Arg$^8$-Pro$^9$-
DAla$^{10}$NH$_2$ (c) NAc-D2Nal$^1$-D4ClPhe$^2$-D3Pal$^3$-Ser$^4$-NMeTyr$^5$-DLys
(N-epsilon-Gly-3-Quinolinyl)$^6$-Leu$^7$-Arg$^8$-Pro$^9$-
DAla$^{10}$NH$_2$ (d) NAc-D2Nal$^1$-D4ClPhe$^2$-D3Pal$^3$-Ser$^4$-NMeTyr$^6$-DLys
(N-epsilon-Gly-4-Quinolinyl)$^6$-Leu$^7$-Arg$^8$-Pro$^9$-
DAla$^{10}$NH$_2$; R$_t$=18.21 min; FAB Mass spec. m/e 1629
(M+H)$^+$. Amino Acid Anal: 1.01 Ala; 0.97 Pro; 0.95 Arg;
0.97 Leu; 1.04 Lys; 1.39 NMeTyr; 0.54 Ser; 0.93 3Pal;
0.98 4ClPhe.

(e) NAc-D2Nal$^1$-D4ClPhe$^2$-D3Pal$^3$-Ser$^4$-NMeTyr$^6$-DLys
(N-epsilon-Gly-2-Pyrazinecarbonyl)$^6$-Leu$^7$-Arg$^8$-Pro$^9$-
DAla$^{10}$NH$_2$; R$_t$=20.0 min; FAB Mass spec. m/e 1578
(M+H)$^+$. Amino Acid Anal: 1.02 Ala; 0.99 Pro; 0.88 Arg;
0.99 Leu; 0.94 Lys; 0.99 Gly; 0.97 NMeTyr; 0.38 Ser;
1.05 3Pal; 1.11 4ClPhe.

(f) NAc-D2Nal$^1$-D4ClPhe$^2$-D3Pal$^3$-Ser$^4$-NMeTyr$^6$-DLys
(N-epsilon-Gly-2-Tetrahydrofuroyl)$^6$-Leu$^7$-Arg$^8$-Pro$^9$-
DAla$^{10}$NH$_2$; R$_t$=21.51 min; FAB Mass spec, m/e 1570
(M+H)$^+$. Amino Acid Anal: 1.04 Ala; 0.95 Pro; 0.95 Arg;
0.97 Leu; 1.02 Lys; 1.06 Gly; 1.21 NMeTyr; 0.50 Ser;
0.93 3Pal; 0.98 4ClPhe.

EXAMPLE 52

NAc-D2-Nal$^1$-D4ClPhe$^2$-D3Pal$^3$-Ser$^4$-NMeTyr$^5$-DOrn
(N-epsilon-Azagly-2-Furoyl)$^6$-Leu$^7$-Lys(N-epsilon-
Isopropyl)$^8$-Pro$^9$-DAla$^{10}$NH$_2$ Using the procedure described in Example 2 but substituting BOC-DOrn(FMOC) for BOC-DLys(FMOC), after work-up, HPLC purification, and lyophilization. NAc-D2Nal$^1$-D4ClPhe$^2$-D3Pal$^3$-Ser$^4$-NMeTyr$^5$-DOrn(N-epsilon-Azagly-Fur-2-oyl)$^6$-Leu$^7$-Lys(N-epsilon-Isopropyl)$^8$-Pro$^9$-DAla$^{10}$NH$_2$ was obtained as the trifluoroacetate salt; R$_t$=28.55 min; FAB Mass spec. m/e 1567 (M+H)$^+$. Amino Acid Anal: 1.02 Ala; 0.96 Pro; 0.94 Lys(Isp); 1.00 Leu; 0.99 Ore; 0.89 NMeTyr; 0.51 Ser; 1.01 3Pal; 0.99 4ClPhe.

EXAMPLE 53

Using the procedure described in Example 52 but substituting the appropriate acid hydrazides for 2-furoic hydrazide, after work-up, HPLC purification, and lyophilization the following compounds are obtained as the trifluoroacetate salts:

(a) NAc-D2Nal$^1$-D4ClPhe$^2$-D3Pal$^3$-Ser$^4$-NMeTyr$^5$-DOrn
(N-epsilon-Azagly-Nicotinyl)$^6$-Leu$^7$-Lys(N-epsilon-
Isopropyl)$^8$-Pro$^9$-DAla$^{10}$NH$_2$; R$_t$=25.45 min; FAB Mass
spec. m/e 1579 (M+H)$^+$. Amino Acid Anal: 1.02 Ala; 0.99
Pro; 1.05 Lys(Isp); 0.99 Leu; 0.99 Orn; 1.01 NMeTyr;
0.54 Ser; 0.96 3Pal; 1.01 4ClPhe.

(b) NAc-D2Nal$^1$-D4ClPhe$^2$-D3Pal$^3$-Ser$^4$-NMeTyr$^5$-DOrn
(N-epsilon-Azagly-Shikimyl)$^6$-Leu$^7$-Lys(N-epsilon-
Isopropyl)$^8$-Pro$^9$-DAlaI-NH$_2$ (c) NAc-D2Nal$^1$-D4ClPhe$^2$-D3Pal$^3$-Ser$^4$-NMeTyr$^5$-DOrn
(N-epsilon-Azagly-quinoline-3-carbonyl)-Leu-Lys(N-
epsilon -Isopropyl)-Pro-DAlaNH$_2$ (d) NAc-D2Nal$^1$-D4ClPhe$^2$-D3Pal$^3$-Ser$^4$-NMeTyr$^5$-DOrn
(N-epsilon-Azagly-Pyridine-3-acetyl)$^6$-Leu$^7$-Lys(N-
epsilon-Isopropyl)$^8$-Pro$^9$-DAla$^{10}$NH$_2$ (e) NAc-D2Nal$^1$-D4ClPhe$^2$-D3Pal$^3$-Ser$^4$-NMeTyr$^5$-DOrn
(N-epsilon-Azagly-Salicyl)$^6$-Leu$^7$-Lys(N-epsilon-
Isopropyl)$^8$-Pro$^9$-DAla$^{10}$NH$_2$ (f) NAc-D2Nal$^1$-D4ClPhe$^2$-D3Pal$^3$-Ser$^4$-NMeTyr$^5$-DOrn
(N-epsilon-Azagly-Benzoyl)$^6$-Leu$^7$-Lys(N-epsilon-
Isopropyl)$^8$-Pro$^9$-DAla$^{10}$NH$_2$ (g) NAc-D2Nal$^1$-D4ClPhe$^2$-D3Pal$^3$-Ser$^4$-NMeTyr$^5$-DOrn
(N-epsilon-Azagly-Formyl)$^6$-Leu$^7$-Lys(N-epsilon-
Isopropyl)$^8$-Pro$^9$-DAla$^{10}$NH$_2$ (h) NAc-D2Nal$^1$-D4ClPhe$^2$-D3Pal$^3$-Ser$^4$-NMeTyr$^5$-DOrn
(N-epsilon-Azagly-Acetyl)$^6$-Leu$^7$-Lys(N-epsilon-
Isopropyl)$^8$-Pro$^9$-DAla$^{10}$NH$_2$ (i) NAc-D2Nal$^1$-D4ClPhe$^2$-D3Pal$^3$-Ser$^4$-NMeTyr$^5$-DOrn
(N-epsilon-Azagly-Picolinyl)$^6$-Leu$^7$-Lys(N-epsilon-
Isopropyl)$^8$-Pro$^9$-DAla$^{10}$NH$_2$ (j) NAc-D2Nal$^1$-D4ClPhe$^2$-D3Pal$^3$-Ser$^4$-NMeTyr$^5$-DOrn
(N-epsilon-Azagly-Isonicotinyl)$^6$-Leu$^7$-Lys(N-epsilon-
Isopropyl)$^8$-Pro$^9$-DAla$^{10}$NH$_2$

EXAMPLE 54

NAc-D2Nal$^1$-D4ClPhe$^2$-D3Pal$^3$-Ser$^4$-NMeTyr$^5$-DOrn
(N-epsilon-Gly-Nicotinyl)$^6$-Leu$^7$-Lys(N-epsilon-Isopropyl)$^8$-Pro$^9$-DAla$^{10}$NH$_2$ The procedure described in Example 1 was used but sustituting Boc-DOrn(Fmoc) for BocDLys(Fmoc). After workup, HPLC purification and lyophlization NAc-D2Nal$^1$-D4ClPhe$^2$-D3Pal$^3$-Ser$^4$-NMeTyr$^5$-DOrn(N-epsilon-Gly-Nicotinyl)$^6$-Leu$^7$-Lys(N-epsilon-Isopropyl)$^8$-Pro$^9$-DAla$^{10}$NH$_2$ was obtained as the trifluoroacetate salt; R$_t$=29.03 min; FAB Mass spec. m/e 1578 (M+H)$^+$. Amino Acid Anal: 1.01 Ala; 0.98 Pro; 1.05 Lys(Isp); 0.99 Leu; 0.99 Orn; 1.01 Gly; 0.99 NMeTyr; 0.51 Ser; 0.96 3Pal; 0.96 4ClPhe.

EXAMPLE 55

Using the procedure described in Example 54 but substituting the appropriate acids for nicotinic acid, after work-up, HPLC purification, and lyophilization the following compounds are obtained as the trifluoroacetate salts:

(a) NAc-D2Nal$^1$-D4ClPhe$^2$-D3Pal$^3$-Ser$^4$-NMeTyr$^5$-DOrn
(N-epsilon-Gly-2-Furoyl)$^6$-Leu$^7$-Lys(N-epsilon-
Isopropyl)$^8$-Pro$^9$-DAla$^{10}$NH$_2$ (b) NAc-D2Nal$^1$-D4ClPhe$^2$-D3Pal$^3$-Ser$^4$-NMeTyr$^5$-DOrn
(N-epsilon-Gly-3-Furoyl)$^6$-Leu$^7$-Lys(N-epsilon-
Isopropyl)$^8$-Pro$^9$-DAla$^{10}$NH$_2$ (c) NAc-D2Nal$^1$-D4ClPhe$^2$-D3Pal$^3$-Ser$^4$-NMeTyr$^5$-DOrn
(N-epsilon-Gly-Shikimyl)$^6$-Leu$^7$-Lys(N-epsilon-
Isopropyl)$^8$-Pro$^9$-DAla$^{10}$NH$_2$ (d) NAc-D2Nal$^1$-D4ClPhe$^2$-D3Pal$^3$-Ser$^4$-NMeTyr$^5$-DOrn
(N-epsilon-Gly-Quinoline-3-carbonyl)$^6$-Leu$^7$-Lys(N-
epsilon-Isopropyl)$^8$-Pro$^9$-DAla$^{10}$NH$_2$(e)

NAc-D2Nal$^1$-D4ClPhe$^2$-D3Pal$^3$-Ser$^4$-NMeTyr$^5$-DOrn(N-
epsilon-Gly-Pyridine-3-acetyl)$^6$-Leu-$^7$Lys(N-epsilon-
Isopropyl)$^8$-Pro$^9$-DAla$^{10}$NH$_2$ (f) NAc-D2Nal¹-D4ClPhe²-D3Pal³-Ser⁴-NMeTyr⁵-DOrn
(N-epsilon-Gly-Picolinyl)⁶-Leu⁷-Lys(N-epsilon-Isopropyl)⁸-Pro⁹-DAla¹⁰NH₂

(g) NAc-D2Nal¹-D4ClPhe²-D3Pal³-Ser⁴-NMeTyr⁵-DOrn
(N-epsilon-Gly-Isonicotinyl)⁶-Leu⁷-Lys(N-epsilon-isopropyl)⁸-Pro⁹-DAla¹⁰NH₂

(h) NAc-D2Nal¹-D4ClPhe²-D3Pal³-Ser⁴-NMeTyr⁵-DOrn
(N-epsilon-Gly-Benzofuran-3-carbonyl)⁶-Leu⁷-Lys(N-epsilon-Isopropyl)⁸-Pro⁹-DAla¹⁰NH₂

(i) NAc-D2Nal¹-D4ClPhe²-D3Pal³-Ser⁴-NMeTyr⁵-DOrn
(N-epsilon-Gly-Benzoyl)⁶-Leu⁷-Lys(N-epsilon-Isopropyl)⁸-Pro⁹-DAla¹⁰NH₂

(j) NAc-D2Nal¹-D4ClPhe²-D3Pal³-Ser⁴-NMeTyr⁵-DOrn
(N-epsilon-Gly-Acetyl)⁶-Leu⁷-Lys(N-epsilon-Isopropyl)⁸-Pro⁹-DAla¹⁰NH₂

(k) NAc-D2Nal¹-D4ClPhe²-D3Pal³-Ser⁴-NMeTyr⁵-DOrn
(N-epsilon-Gly-Salicyl)⁶-Leu⁷-Lys(N-epsilon-Isopropyl)⁸-Pro⁹-DAla¹⁰NH₂

(l) NAc-D2Nal¹-D4ClPhe²-D3Pal³-Ser⁴-NMeTyr⁵-DOrn
(N-epsilon-6-Methyl-nicotinyl)⁶-Leu-⁷Lys(N-epsilon-Isopropyl)⁸-Pro⁹-DAla¹⁰NH₂

(m) NAc-D2Nal¹-D4ClPhe²-D3Pal³-Ser⁴-NMeTyr⁵-DOrn
(N-epsilon-Gly-2Methylnicotinyl)⁶-Leu⁷-Lys(N-epsilon-Isopropyl)⁸-Pro⁹-DAla¹⁰NH₂

EXAMPLE 56

Using the procedure described in Example 37 but the appropriate acid hydrazides for 2-furoic hydrazide, after work-up, HPLC purification, and lyophilization the following compounds are obtained as the trifluoroacetate salts:

(a) NAc-D2Nal¹-D4ClPhe²-D3Pal³-Ser⁴-NMeTyr⁵-DLys
(N-epsilon-Azagly-Shikimyl)⁶-Leu⁷-Arg⁸-Pro⁹-DAla¹⁰NH₂.

(b) NAc-D2Nal¹-D4ClPhe²-D3Pal³-Ser⁴-NMeTyr⁵-DLys
(N-epsilon-Azagly-Quinoline-3-carbonyl)⁶-Leu⁷-Arg⁸-Pro⁹-DAla¹⁰NH₂.

(c) NAc-D2Nal¹-D4ClPhe²-D3Pal³-Ser⁴-NMeTyr⁵-DLys
(N-epsilon-Azagly-2-Pyridine-3-acetyl)⁶-Leu⁷-Arg⁸-Pro⁹-DAla¹⁰NH₂.

(d) NAc-D2Nal¹-D4ClPhe²-D3Pal³-Ser⁴-NMeTyr⁵-DLys
(N-epsilon-Azagly-Salicyl)⁶-Leu⁷-Arg⁸-Pro⁹-DAla¹⁰NH₂.

(e) NAc-D2Nal¹-D4ClPhe²-D3Pal³-Ser⁴-NMeTyr⁵-DLys
(N-epsilon-Azagly-Furoyl)⁶-Leu⁷-Arg⁸-Pro⁹-DAla¹⁰NH₂.

(f) NAc-D2Nal¹-D4ClPhe²-D3Pal³-Ser⁴-NMeTyr⁵-DLys
(N-epsilon-Azagly-Isonicotinyl)⁶-Leu⁷-Arg⁸-Pro⁹-DAla¹⁰NH₂.

(g) NAc-D2Nal¹-D4ClPhe²-D3Pal³-Ser⁴-NMeTyr⁵-DLys
(N-epsilon-Azagly-Thiophene-2-carbonyl)⁶-Leu⁷-Arg⁸-Pro⁹-DAla¹⁰NH₂.

(h) NAc-D2Nal¹-D4ClPhe²-D3Pal³-Ser⁴-NMeTyr⁵-DLys
(N-epsilon-Azagly-Benzoyl)⁶-Leu⁷-Arga-Pro⁹-DAla¹⁰NH₂.

EXAMPLE 57

The procedure described in Example 1 was used but substituting the appropriate acids and amino acids for nicotinic acid. After workup and HPLC purification the following compounds were obtained:

(a) NAcD2Nal¹-D4ClPhe²-D3Pal³-Ser⁴-NMeTyr⁵-DLys(N-epsilon-Gly-Gly-furoyl)⁶-Leu⁷-Lys(Isp)⁸-Pro⁹-DAla¹⁰NH₂; $R_t$=26.64 min; FAB Mass spec. m/e 1638 (M+H)⁺. Amino Acid Anal: 1.04 Ala; 1.00 Pro; 0.83 Lys(Isp); 0.98 Leu; 1.00 Lys; 1.96 Gly; 0.93 NMeTyr; 0.55 Ser; 0.95 3Pal; 1.04 4ClPhe.

(b) NAc-D2Nal¹-D4ClPhe²-D3Pal³-Ser⁴-NMeTyr⁵-DLys
(N-epsilon-5-aminocaproyl-furoyl)⁶-Leu⁷-Lys(Isp)⁸-Pro⁹-DAla¹⁰NH₂; $R_t$=28.20 min; FAB Mass spec. m/e 1636 (M+H)⁺. Amino Acid Anal: 1.05 Ala; 1.02 Pro; 0.94 Lys(Isp); 0.99 Leu; 0.95 Lys; 0.84 NMeTyr; 0.55 Ser; 1.07 3Pal; 0.99 4ClPhe.

(c) NAc-D2Nal¹-D4ClPhe²-D3Pal³-Ser⁴-NMeTyr⁵-DLys
(N-epsilon-beta-alanyl-glycyl-furoyl)⁶-Leu⁷-Lys(Isp)⁸-Pro⁹-DAla¹⁰NH₂; $R_t$=26.83 min; FAB Mass spec. m/e 1652 (M+H)⁺. Amino Acid Anal: 1.08 Ala; 1.02 Pro; 0.94 Lys(Isp); 1.00 Leu; 0.97 Lys; 0.77 Gly; 0.84 NMeTyr; 0.64 Ser; 1.09 3Pal; 1.08 4ClPhe.

(d) NAc-D2Nal¹-D4ClPhe²-D3Pal³-Ser⁴-NMeTyr⁵-DLys
(N-epsilon-5-aminocaproyl-glycyl-furoyl)⁶-Leu⁷-Lys(Isp)⁸-Pro⁹-DAla¹⁰NH₂; $R_t$=27.68 min; FAB Mass spec. m/e 1693 (M+H)⁺. Amino Acid Anal: 1.04 Ala; 1.03 Pro; 0.92 Lys(Isp); 1.01 Leu; 0.92 Lys; 0.77 Gly; 0.92 NMeTyr; 0.33 Ser; 1.07 3Pal; 0.96 4ClPhe.

(e) NAc-D2Nal¹-D4ClPhe²-D3Pal³-Ser⁴-NMeTyr⁵-DLys
(N-epsilon-4-aminobutyryl-glycyl-furoyl)⁶-Leu⁷-Lys(Isp)⁸-Pro⁹-DAla¹⁰NH₂; $R_t$=18.02 min; FAB Mass spec. m/e 1665 (M+H)⁺. Amino Acid Anal: 0.98 Ala; 1.01 Pro; 1.2 Lys(Isp); 0.98 Leu; 1.03 Lys; 0.74 Gly; 1.06 NMeTyr; 0.36 Ser; 1.14 3Pal; 1.16 4ClPhe.

EXAMPLE 58

NAc-D2Nal¹-D4ClPhe²-D3Pal³-Ser⁴-NMeTyr⁵-DLys(N-epsilon-Azagly-Propionyl)⁶-Leu⁷-Lys(N-epsilon-Isopropyl)⁸-Pro⁹-DAla¹⁰NH₂

The procedure described in Example 2 was used but subdtituting propionyl hydrazide for 2-furoic hydrazide. After workup, HPLC purification and lyophlization NAc-D2Nal¹-D4ClPhe²-D3Pal³-Ser⁴-NMeTyr⁵-DLys(N-epsilon-Azagly-Propionyl)⁶-Leu⁷-Lys(N-epsilon-Isopropyl)⁸-Pro⁹-DAla¹⁰NH₂ was obtained as the trifluoroacetate salt; $R_t$=16.21 min; FAB Mass spec. m/e 1543 (M+H)⁺. Amino Acid Anal: 0.99 Ala; 1.01 Pro; 1.24 Lys(Isp); 1.00 Leu; 1.00 Lys; 1.03 NMeTyr; 0.50 Ser; 1.14 3Pal; 0.90 4ClPhe.

EXAMPLE 59

NAc-D2Nal¹-D4ClPhe²-D3Pal³-Ser⁴-NMeTyr⁵-DLys(N-epsilon-Azagly-Fur-2-oyl)⁶-Leu⁷-Lys(N-epsilon-Isopropyl)⁸-Pro⁹-Sar¹⁰NH₂

The procedure described in Example 2 was used but subdtituting Boc-Sar-NH-resin for Boc-DAlaNH-resin. After workup, HPLC purification and lyophlization NAc-D2Nal¹-D4ClPhe²-D3Pal³-Ser⁴-NMeTyr⁵-DLys(N-epsilon-Azagly-Fur-2-oyl)⁶-Leu⁷-Lys(N-epsilon-Isopropyl)⁸-Pro⁹-Sar10NH₂ was obtained as the trifluoroacetate salt; $R_t$=19.13 min; FAB Mass spec. m/e 1581 (M+H)⁺. Amino Acid Anal: 1.01 Sar; 0.98 Pro; 1.19 Lys(Isp); 1.01 Leu; 1.01 Lys; 1.09 NMeTyr; 0.54 Ser; 1.14 3Pal; 1.31 4ClPhe.

EXAMPLE 60

NAc-D2Nal¹-D4ClPhe²-D3Pal³-Ser⁴-NMeTyr⁵-DLys(N-epsilon-Azagly-Nicotinyl)⁶-Leu⁷-Lys(N-epsilon-Isopropyl)⁸-Pro⁹-Sar¹⁰NH₂

The procedure described in Example 3 was used but subdtituting Boc-Sar-NH-resin for Boc-DAlaNH-resin. After workup, HPLC purification and lyophlization NAc-D2Nal¹-D4ClPhe²-D3Pal³-Ser⁴-NMeTyr⁵-DLys(N-epsilon-Azagly-Fur-2-oyl)⁶-Leu⁷-Lys(N-epsilon-Isopropyl)⁸-Pro⁹-Sar10NH₂ was obtained as the trifluoroacetate salt; $R_t$=16.26 min; FAB Mass spec. m/e 1592 (M+H)⁺. Amino Acid Anal: 1.01 Sar; 0.98 Pro; 1.15 Lys(Isp); 1.00 Leu; 1.01 Lys; 1.04 NMeTyr; 0.54 Ser; 1.13 3Pal; 1.31 4ClPhe.

EXAMPLE 61

NAc-D2Nal¹-D4ClPhe²-D3Pal³-Ser⁴-NMeTyr⁵-DLys(N-epsilon-N'-Carbonyl-Diaminoethane-N"-Fur-2-oyl)⁶-Leu⁷-Lys(N-epsilon-Isopropyl)⁸-Pro⁹-DAla¹⁰NH₂

The procedure described in Example 14 was used but subdtituting Boc-Lys(Isp,Cbz) for Boc-Arg(Tos). After workup, HPLC purification and lyophlization NAc-D2Nal¹-D4ClPhe²D3Pal³-Ser⁴NMeTyr⁵-DLys(N-epsilon-N'-Carbonyl-Diaminoethane-N"-Fur-2-oyl)⁶-Leu⁷-Lys(N-epsilon-Isopropyl)⁸-Pro⁹-DAla¹⁰NH₂ was obtained as the trifluoroacetate salt; $R_t$=27.55 min; FAB Mass spec. m/e 1609 (M+H)⁺. Amino Acid Anal: 1.02 Ala; 1.00 Pro; 1.07 Lys(Isp); 0.99 Leu; 0.98 Lys; 0.76 NMeTyr; 0.48 Ser; 0.96 3Pal; 1.01 4ClPhe.

EXAMPLE 62

NAc-D2Nal¹-D4ClPhe²-D3Pal³-Ser⁴-NMeTyr⁵-DLys(N-epsilon-N'-Carbonyl-Diaminoethane-N"-Nicotinyl)⁶-Leu⁷-Lys(N-epsilon-Isopropyl)⁸-Pro⁹-DAla¹⁰NH₂

The procedure described in Example 61 was used but subdtituting nicotinic acid for 2-furoic acid. After workup, HPLC purification and lyophlization NAc-D2Nal¹-D4ClPhe²-D3Pal³-Ser⁴-NMeTyr⁵-DLys(N-epsilon-N'-Carbonyl-Diaminoethane-N"-nicotinyl)⁶-Leu⁷-Lys(N-epsilon-Isopropyl)⁸-Pro⁹-DAla¹⁰NH₂ was obtained as the trifluoroacetate salt; $R_t$=22.08 min; FAB Mass spec. m/e 1620 (M+H)⁺. Amino Acid Anal: 1.01 Ala; 0.99 Pro; 1.05 Lys(Isp); 0.99 Leu; 1.01 Lys; 0.87 NMeTyr; 0.48 Ser; 0.96 3Pal; 1.01 4ClPhe.

EXAMPLE 63

NAc-D2Nal¹-D4ClPhe²-D3Pal³-Ser⁴-NMePhe(Atz)⁵-DLys(N-epsilon-N'-Gly-Atz)⁶-Leu⁷-Lys(N-epsilon-Isopropyl)⁸-Pro⁹-DAla¹⁰NH₂

The procedure described in Example 45 was used but instead of coupling with nicotinic acid the resin was first treated with diphenyl cyanocarbonimidate in DMF for 16 h and then with hydrazine for 8h. After workup, HPLC purification and lyophlization NAc-D2Nal¹-D4ClPhe²-D3Pal³-Ser⁴-NMePhe(Atz)⁵-DLys(N-epsilon-N'-Gly-Atz)⁶-Leu⁷-Lys(N-epsilon-Isopropyl)⁸-Pro⁹-DAla¹⁰NH₂ was obtained as trifluoroacetate salt; $R_t$=13.22 min; FAB Mass spec. m/e 1649 (M+H)⁺. Amino Acid Anal: 1.00 Ala; 1.00 Pro; 0.9 Lys(Isp); 1.0 Leu; 0.3 Gly; 1.00Lys; 0.50 Ser; 1.10 3Pal; 1.3 4ClPhe.

EXAMPLE 64

NAc-D2Nal¹-D4ClPhe²-D3Pal³-Ser⁴-NMeTyr⁵-DLys(N-epsilon-Gly-Biotinyl)⁶-Leu⁷-Lys(N-epsilon-isopropyl)⁸-Pro⁹-DAla¹⁰NH₂

The procedure described in Example 1 was used but substituting biotin for nicotinic acid. After workup, HPLC purification and lyophlization NAc-D2Nal¹-D4ClPhe²-D3Pal³-Ser⁴-NMeTyr⁵-DLys(N-epsilon-Gly-Biotinyl)⁶-Leu⁷-Lys(N-epsilon-Isopropyl)⁸-Pro⁹-DAla¹⁰NH₂ was obtained as trifluoroacetate salt; $R_t$=21.5 min; FAB Mass spec. m/e 1712 (M+H)⁺. Amino Acid Anal: 1.00 Ala; 0.98 Pro; 1.2 Lys(Isp); 1.01 Leu; 0.89 Gly; 1.02 Lys; 0.31 Ser; 1.09 3Pal; 1.2 4ClPhe.

EXAMPLE 65

The procedure described in Example 17 was used but substituting The appropriate amino acids and acids. After workup, HPLC purification and lyophlization the following compounds were obtained:

(a) NAc-D2Nal¹-D4ClPhe²-D3Pal³-Ser⁴-NMeTyr⁵-DLys(N-epsilon-DTrp(Formyl)-Shikimyl)⁶-Leu⁷-Arg⁸-Pro⁹-DAla¹⁰NH₂ was obtained as trifluoroacetate salt; $R_t$=19.97 min; FAB Mass spec. m/e 1786 (M+H)⁺. Amino Acid Anal: 1.02 Ala; 0.99 Pro; 0.96 Arg; 0.97 Leu; 1.06 Lys; 1.37 NMeTyr; 0.51 Ser; 0.95 3Pal; 0.97 4ClPhe.

(b) NAc-D2Nal¹-D4ClPhe²-D3Pal³-Ser⁴-NMeTyr⁵-DLys(N-epsilon-DSer-3Furoyl)⁶-Leu⁷-Arg⁸-Pro⁹-DAla¹⁰NH₂ was obtained as trifluoroacetate salt; $R_t$=20.59 min; FAB Mass spec. m/e 1596 (M+H)⁺. Amino Acid Anal: 1.06 Ala; 1.01 Pro; 0.95 Arg; 1.02 Leu; 0.95 Lys; 1.18 NMeTyr; 0.88 Ser; 0.95 3Pal; 1.06 4ClPhe.

(c) NAc-D2Nal¹-D4ClPhe²-D3Pal³-Ser⁴-NMeTyr⁵-DLys(N-epsilon-Gly-3Pyridylacetyl)⁶-Leu⁷-Arg⁸-Pro⁹-DAla¹⁰NH₂ was obtained as trifluoroacetate salt; $R_t$=16.05 min; FAB Mass spec. m/e 1592 (M+H)⁺. Amino Acid Anal: 1.02 Ala; 1.00 Pro; 0.98 Arg; 1.01 Leu; 0.95 Lys; 0.97 Gly; 1.18 NMeTyr; 0.36 Ser; 1.08 3Pal; 1.14 4ClPhe.

We claim:

1. A peptide or pharmaceutically acceptable salt thereof of the formula

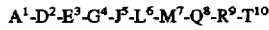

$$A^1-D^2-E^3-G^4-J^5-L^6-M^7-Q^8-R^9-T^{10}$$

wherein

A is an aminoacyl residue selected from the group consisting of
N-acetyl-D-3-(naphth-2-yl)alanyl,
N-acetyl-D-phenylalanyl,
N-acetyl-D-3-(4-chlorophenyl)alanyl,
N-acetyl-D-3-(quinolin-3-yl)alanyl,
N-acetyl-azaglycyl, and
N-acetylsarcosyl;

D is an aminoacyl residue selected from the group consisting of
D-phenylalanyl,
D-3-(4-chlorophenyl)alanyl,
D-3-(4-fluorophenyl)alanyl, and
D-3-(naphth-2-yl)alanyl;

E is an aminoacyl residue selected from the group consisting of
D-3-(pyrid-3-yl)alanyl,
D-3-(naphth-1-yl)alanyl,
N-acetyl-D-3-(quinolin-3-yl)alanyl,
D-3-(thiazol-2-yl)alanyl, and
D-3-(benzo(b)thien-2-yl)alanyl;

G is an aminoacyl residue selected from the group consisting of
L-seryl,
L-seryl(O-benzyl), and
N(R¹)-L-seryl where R¹- is hydrogen or alkyl of from one to four carbon atoms;

J is an aminoacyl residue selected from the group consisting of
N(R¹)-L-(3-(4-(3-amino-1,2,4-triazol-5-yl)aminophenyl))alanyl;
N(R¹)-L-(3-(4-(3-amino-1,2,4-triazol-5-1)aminocyclohexyl))alanyl;
N(R¹)-L-(3-(4-nicotinyl)aminocyclohexyl))alanyl;
N(R¹)-(N-epsilon-nicotinyl)-L-lysyl; N(R¹)-(N-epsilon-(3-amino-1,2,4-triazol-5-yl))L-lysyl;
N(R¹)-L-(3-(4-nitrophenyl))alanyl; L-(3-(4-aminophenyl))alanyl;
L-(3-(4-aminocyclohexyl))alanyl;
N(R¹)-L-tyrosyl;
N(R¹)-L-tyrosyl(O-methyl);

N(R¹)-L-phenylalanyl;
N(R¹)-L-cyclohexylalanyl;
N(R¹)-L-arginyl; and
N(R¹)-L-homoarginyl;

where R¹ is as defined above;

L is a D-aminoacyl residue having the structure

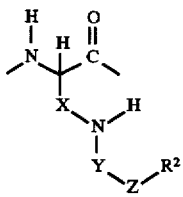

where

X is selected from the group consisting of —(CH$_2$)$_n$— where n is an integer of from one to six, inclusive, and

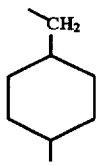

Y is an aminoacyl residue selected from the group consisting of
D-3-(benzo(b)thien-2-yl)alanyl,
L-3-(benzo(b)thien-2-yl)alanyl,
D-3-(4-chlorophenyl)alanyl,
D-cyclohexylalanyl,
D-histidyl,
D-histidyl (benzyl)
D-3-(naphth-2-yl)alanyl,
D-phenylalanyl,
D-3-(pyrid-3-yl)alanyl,
sarcosyl,
L-seryl,
D-seryl,
D-threonyl,
D-3-(thiazol-4-yl)alanyl,
D-tryptyl,
D-tyrosyl,
D-tyrosyl(O-methyl), and Z is absent or is an aminoacyl residue selected from the group consisting of
D-alanyl,
L-alanyl,
azaglycyl,
D-cyclohexylalanyl,
glycyl,
D-histidyl,
D-phenylalanyl,
D-3(-4-(3-amino-1,2,4-triazol-5-yl)phenyl)alanyl;
sarcosyl,
D-seryl,
L-seryl, and

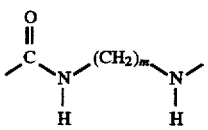

where
m is an integer of from one to twelve, inclusive; and
R² is 3-amino-1,2,4-triazol-5-yl or an acyl group selected from the group consisting of acetyl,
(4-acetylpiperazin-1-yl)carbonyl,
(adamant-1-yl)carbonyl,
benzoyl optionally substituted with a group selected from alkyl of one to four carbon atoms, alkoxy of one to four carbon atoms, and halogen,
biotinyl,
dihydroshikimyl,
formyl,
2- and 6-hydroxynicotinyl,
(indolyl)carbonyl,
(4-methylpiperazinol-1-yl)carbonyl,
(morpholin-1-yl)carbonyl,
2- and 6-methylnicotinyl,
1- and 2-naphthoyl optionally substituted with a group selected from alkyl of one to four carbon atoms, alkoxy of one to four carbon atoms, and halogen,
(piperazin-1-yl)carbonyl,
propionyl,
pyrazinoyl,
(pyrrolyl)carbonyl,
(quinolinyl)carbonyl,
salicilyl,
shikimyl,
2-(tetrahydrofuroyl), and
(thien-2-yl)carbonyl;

M is an aminoacyl residue selected from the group consisting of
L-leucyl,
N(R¹)-L-leucyl,
L-valyl,
L-cyclohexylalanyl, and
N(R¹)-L-cyclohexylalanyl,
where
R¹ is as defined above;

Q is an aminoacyl residue selected from the group consisting of
L-citrullyl,
L-homocitrullyl,
L-(epsilon-N-isopropyl)lysyl,
L-arginyl,
N(R¹)-L-arginyl,
L-homoarginyl,
L-2-amino-6-N$^G$-ethylguanidinohexanoyl, and L-2-amino-6-N$^G$,N$^G$-diethylguanidinohexanoyl,
where
R¹ is as defined above;

R is an aminoacyl residue selected from the group consisting of
L-Prolyl, and
N(R¹)-L-alanyl,
where
R¹ is as defined above; and
T is —NH(CH$_2$CH$_3$) or is an aminoacyl residue selected from the group consisting of D-alanylamide,
N($R^1$)-L-alaninamide,
N($R^1$)-D-alaninamide,
sarcosamide,
D-serylamide, and
azaglycylamide,
where
$R^1$ is as defined above and with the proviso that when T is —NH(CH$_2$CH$_3$) then R is L-prolyl.

2. A decapeptide as defined by claim 1 wherein Z is absent.

3. A decapeptide as defined by claim 1 wherein
A is an aminoacyl residue selected from the group consisting of
  N-acetyl-D-3-(quinolin-3-yl)alanyl, and N-acetyl-D-3-(naphth-2-yl)alanyl;
D is D-3-(4-chlorophenyl)alanyl;
E is D-3-(pyrid-3-yl)alanyl;
G is L-seryl;
J is an aminoacyl residue selected from the group consisting of
  N($R^1$)-L-(3-(4-(3-amino-1,2,4-triazol-5-yl)aminophenyl))alanyl;
  N($R^1$)-L-(3-(4-(3-amino-1,2,4-triazol-5-yl)aminocyclohexyl))alanyl;
  N($R^1$)-L-(3-(4-nicotinyl)aminocyclohexyl))alanyl;
  N($R^1$)-(N-epsilon-nicotinyl)-L-lysyl; N($R^1$)-(N-epsilon-(3-amino-1,2,4-triazol-5-yl))L-lysyl;
  N($R^1$)-L-(3-(4-nitrophenyl))alanyl; L-(3-(4-aminophenyl))alanyl;
  L-(3-(4-aminocyclohexyl))alanyl;
  N($R^1$)-L-tyrosyl;
  N($R^1$)-L-tyrosyl(O-methyl);
  N($R^1$)-L-phenylalanyl;
  N($R^1$)-L-cyclohexylalanyl;
  N($R^1$)-L-arginyl; and
  N($R^1$)-L-homoarginyl;
M is N($R^1$)-L-leucyl where $R^1$ is as defined therein;
Q is an aminoacyl residue selected from the group consisting of
  L-citrullyl,
  L-homocitrullyl,
  L-(epsilon-N-isopropyl)lysyl,
  L-arginyl,
  N($R^1$)-L-arginyl,
  L-homoarginyl,
  L-2-amino-6-$N^G$-ethylguanidinohexanoyl, and L-2-amino-6-$N^G$,$N^{G'}$-diethylguanidinohexanoyl;
R is L-prolyl; and
T is D-alaninamide.

4. NAc-D2Nal$^1$-D4ClPhe$^2$-D3Pal$^3$-Ser$^4$-NMeTyr$^5$-DLys(N-epsilon-DSer-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-(N'-Carbonyl-Diaminoethane-N"-Nicotinyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-(N'-Carbonyl-Diaminoethane-N"-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DSer-2-Furoyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-(N'-epsilon-Aminocaproyl)(N"-beta-Alanyl)-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-Gly-Gly-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-D3Pal-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(DHis-alpha-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DTyr)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DTyr(OMe)-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-Gly-Azagly-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-(5-Aminovaleryl)-Azagly-Nicotinyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DThr-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DHis-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-D3Pal-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-(N'-Carbonyl-Piperazine-N"-2-Furoyl))$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-(N'-Carbonyl-Diaminopropane-N"-Shikimyl))$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-Sar-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DHis-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-D-3Pal-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DSer-Gly-Shikimyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-DSer-Gly-Nicotinyl)$^6$-Leu$^7$-Arg$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-Gly-Gly-furoyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-beta-alanyl-glycyl-furoyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-5-aminocaproyl-glycyl-furoyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-4-aminobutyryl-glycyl-furoyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-N'-Carbonyl-Diaminoethane-N''-Fur-2-oyl)$^6$-Leu$^7$-Lys(N-epsilon-Isopropyl)$^8$-Pro$^9$-DAla$^{10}$NH$_2$;

NAc-D2Nal$^1$-D4ClPhe$^2$-D3Pal$^3$-Ser$^4$-NMeTyr$^5$-DLys(N-epsilon-N'-Carbonyl-Diaminoethane-N''-Nicotinyl)$^6$-Leu$^7$-Lys(N-epsilon-Isopropyl)$^8$-Pro$^9$-DAla$^{10}$NH$_2$; and NAc-D2Nal$^1$-D4ClPhe$^2$-D3Pal$^3$-Ser$^4$-NMeTyr$^5$-DLys(N-epsilon-DTrp(Formyl)-Shikimyl)$^6$-Leu$^7$-Arg$^8$-Pro$^9$-DAla$^{10}$NH$_2$.

5. A pharmaceutical composition for inhibiting the release of LHRH comprising a therapeutically effective amount of a compound as defined by claim 1 in combination with a pharmaceutically acceptable carrier.

6. A method of inhibiting LHRH release in a mammal in need of such treatment comprising administering to the host animal a therapeutically effective amount of a compound as defined by claim 1.

* * * * *

UNITED STATES PATENT AND TRADEMARK OFFICE
CERTIFICATE OF CORRECTION

PATENT NO. : 5,698,522
DATED : December 16, 1997
INVENTOR(S) : Haviv et al.

It is certified that error appears in the above-identified patent and that said Letters Patent is hereby corrected as shown below:

Column 44, line 23, change "methylpiperazinol" to --methylpiperazin--.

Signed and Sealed this

Seventh Day of April, 1998

Attest:

BRUCE LEHMAN

*Attesting Officer*    *Commissioner of Patents and Trademarks*